US006759519B2

(12) United States Patent
Li et al.

(10) Patent No.: US 6,759,519 B2
(45) Date of Patent: Jul. 6, 2004

(54) ANTIBODIES TO HUMAN G-PROTEIN CHEMOKINE RECEPTOR HDGNR10 (CCR5RECEPTOR)

(75) Inventors: Yi Li, Gaithersburg, MD (US); Steven M. Ruben, Olney, MD (US)

(73) Assignee: Human Genome Sciences, Inc., Rockville, MD (US)

(*) Notice: Subject to any disclaimer, the term of this patent is extended or adjusted under 35 U.S.C. 154(b) by 469 days.

(21) Appl. No.: 09/339,912

(22) Filed: Jun. 25, 1999

(65) Prior Publication Data

US 2002/0099176 A1 Jul. 25, 2002

Related U.S. Application Data

(62) Division of application No. 08/466,343, filed on Jun. 6, 1995, now Pat. No. 6,025,154.

(51) Int. Cl.[7] .................. C07K 16/28; A61K 39/395
(52) U.S. Cl. .................. 530/388.22; 530/387.1; 530/387.3; 530/387.5; 530/387.9; 530/388.1; 530/388.2; 530/388.7; 530/388.73; 530/388.75; 530/389.1; 530/389.6; 424/130.1; 424/133.1; 424/135.1; 424/137.1; 424/139.1; 424/141.1; 424/143.1; 424/144.1; 424/152.1; 424/153.1; 424/154.1; 424/172.1; 424/173.1
(58) Field of Search .................. 530/387.1, 387.3, 530/387.5, 387.9, 388.1, 388.2, 388.22, 388.7, 388.73, 388.75, 389.1, 389.6; 424/130.1, 133.1, 135.1, 137.1, 139.1, 141.1, 143.1, 144.1, 152.1, 153.1, 154.1, 172.1, 173.1

(56) References Cited

U.S. PATENT DOCUMENTS

| | | | |
|---|---|---|---|
| 5,440,021 A | | 8/1995 | Chuntharapai et al. |
| 5,652,133 A | * | 7/1997 | Murphy |
| 5,707,815 A | * | 1/1998 | Charo et al. |
| 5,798,206 A | | 8/1998 | Neurath et al. |
| 5,817,310 A | * | 10/1998 | Ramakrishnan et al. |
| 5,912,176 A | | 6/1999 | Wang |
| 5,919,776 A | | 7/1999 | Hagmann et al. |
| 5,928,881 A | | 7/1999 | Barnette et al. |
| 5,939,320 A | | 8/1999 | Littman et al. |
| 5,939,538 A | | 8/1999 | Leavitt et al. |
| 5,961,976 A | | 10/1999 | Wang |
| 5,962,462 A | | 10/1999 | Mills et al. |
| 5,994,515 A | | 11/1999 | Hoxie |
| 6,013,644 A | | 1/2000 | Mills et al. |
| 6,025,154 A | | 2/2000 | Li et al. |
| 6,057,102 A | | 5/2000 | Landau et al. |
| 6,511,826 B2 | | 1/2003 | Li et al. |
| 2002/0048786 A1 | | 4/2002 | Rosen et al. |
| 2002/0076745 A1 | | 6/2002 | Li et al. |
| 2003/0023044 A1 | | 1/2003 | Li et al. |

FOREIGN PATENT DOCUMENTS

| | | |
|---|---|---|
| CA | 2146328 | 5/1994 |
| CA | 2128308 | 6/1994 |
| EP | 0 671 391 | 9/1995 |
| EP | 0 612 723 | 8/1997 |
| EP | 0 834 564 | 5/1998 |
| EP | 0 979 655 | 2/2000 |
| JP | 10-179180 | 7/1998 |
| JP | 11-243960 | 9/1999 |
| JP | 11-292795 | 10/1999 |
| SU | 2126048 | 2/1999 |
| WO | WO 94/11504 | 5/1994 |
| WO | WO 95/19436 | 7/1995 |
| WO | WO 96/22371 | 7/1996 |
| WO | WO 96/23068 | 8/1996 |
| WO | WO 96/38559 | 12/1996 |
| WO | WO 96/39437 | 12/1996 |
| WO | WO 97/00960 | 1/1997 |
| WO | WO 97/19696 | 6/1997 |
| WO | WO 97/21812 | 6/1997 |
| WO | WO 97/22698 | 6/1997 |
| WO | WO 97/25340 | 7/1997 |
| WO | WO 97/28258 | 8/1997 |
| WO | WO 97/32019 | 9/1997 |
| WO | WO 97/35881 | 10/1997 |
| WO | WO 97/37005 | 10/1997 |
| WO | WO 97/41225 | 11/1997 |
| WO | WO 97/41230 | 11/1997 |
| WO | WO 97/44055 | 11/1997 |
| WO | WO 97/45543 | 12/1997 |
| WO | WO 97/46697 | 12/1997 |
| WO | WO 97/47318 | 12/1997 |
| WO | WO 97/47319 | 12/1997 |
| WO | WO 97/49424 | 12/1997 |
| WO | WO 98/00535 | 1/1998 |

(List continued on next page.)

OTHER PUBLICATIONS

Gomez–Reino et al. Arthritis Rheum. 1999; 42:989–992.*
Mack et al. Arthritis Rheum. 1999;42:981–988.*
Suzuki et al. Int. Immunol. 1999; 11:553–559.*
Skolnick and Fetrow Trends in Biotechnol. 18(1):34–39 2000.*

(List continued on next page.)

*Primary Examiner*—Phillip Gambel
*Assistant Examiner*—Jessica H. Roark
(74) *Attorney, Agent, or Firm*—Sterne, Kessler, Goldstein & Fox P.L.L.C.

(57) ABSTRACT

Antibodies against human G-protein chemokine receptor polypeptides, the polypeptides themselves, DNA (RNA) encoding such polypeptides and a procedure for producing such polypeptides by recombinant techniques are disclosed. Also disclosed are methods for utilizing such polypeptides for identifying antagonists and agonists to such polypeptides and methods of using the agonists and antagonists therapeutically to treat conditions related to the underexpression and overexpression of the G-protein chemokine receptor polypeptides, respectively. Also disclosed are diagnostic methods for detecting a mutation in the G-protein chemokine receptor nucleic acid sequences and detecting a level of the soluble form of the receptors in a sample derived from a host.

84 Claims, 4 Drawing Sheets

FOREIGN PATENT DOCUMENTS

| | | |
|---|---|---|
| WO | WO 98/05798 | 2/1998 |
| WO | WO 98/14480 | 4/1998 |
| WO | WO 98/15569 | 4/1998 |
| WO | WO 98/17308 | 4/1998 |
| WO | WO 98/18826 | 5/1998 |
| WO | WO 98/20166 | 5/1998 |
| WO | WO 98/25604 | 6/1998 |
| WO | WO 98/25605 | 6/1998 |
| WO | WO 98/25617 | 6/1998 |
| WO | WO 98/27815 | 7/1998 |
| WO | WO 98/30218 | 7/1998 |
| WO | WO 98/31364 | 7/1998 |
| WO | WP 98/34945 | 8/1998 |
| WO | WO 98/38212 | 9/1998 |
| WO | WO 98/42354 | 10/1998 |
| WO | WO 98/44158 | 10/1998 |
| WO | WO 98/51705 | 11/1998 |
| WO | WO 98/54317 | 12/1998 |
| WO | WO 98/55873 | 12/1998 |
| WO | WO 98/56421 | 12/1998 |
| WO | WO 98/58536 | 12/1998 |
| WO | WO 98/58966 | 12/1998 |
| WO | WO 99/01127 | 1/1999 |
| WO | WO 99/04794 | 2/1999 |
| WO | WO 99/06561 | 2/1999 |
| WO | WO 99/08703 | 2/1999 |
| WO | WO 99/09984 | 3/1999 |
| WO | WO 99/12416 | 3/1999 |
| WO | WO 99/13112 | 3/1999 |
| WO | WO 99/14378 | 3/1999 |
| WO | WO 99/17773 | 4/1999 |
| WO | FR 2 771 423 | 5/1999 |
| WO | WO 99/23107 | 5/1999 |
| WO | WO 99/23253 | 5/1999 |
| WO | WO 99/24065 | 5/1999 |
| WO | WO 99/24553 | 5/1999 |
| WO | WO 99/27122 | 6/1999 |
| WO | WO 99/27939 | 6/1999 |
| WO | WO 99/28474 | 6/1999 |
| WO | WO 99/32100 | 7/1999 |
| WO | WO 99/32138 | 7/1999 |
| WO | WO 99/33989 | 7/1999 |
| WO | WO 99/36518 | 7/1999 |
| WO | WO 99/38514 | 8/1999 |
| WO | WO 99/43711 | 9/1999 |
| WO | WO 99/46372 | 9/1999 |
| WO | WO 99/51751 | 10/1999 |
| WO | WO 99/53033 | 10/1999 |
| WO | WO 99/62535 | 12/1999 |
| WO | WO 99/66944 | 12/1999 |
| WO | WO 99/67429 | 12/1999 |
| WO | WO 00/02045 | 1/2000 |
| WO | WO 00/05265 | 2/2000 |
| WO | WO 00/06085 | 2/2000 |
| WO | WO 00/06146 | 2/2000 |
| WO | WO 00/06153 | 2/2000 |
| WO | WO 00/08043 | 2/2000 |
| WO | WO 00/09525 | 2/2000 |
| WO | WO 00/10965 | 3/2000 |
| WO | WO 00/14220 | 3/2000 |
| WO | WO 00/15663 | 3/2000 |
| WO | WO 00/15785 | 3/2000 |
| WO | WO 01/58916 | 8/2001 |
| WO | WO 02/064612 | 8/2002 |

OTHER PUBLICATIONS

Murdoch and Finn Blood 95:3032–3043 2000.*
GenBank ref file NP_000570.1 (chemokine receptor 5 [Homo sapeins]) BLAST homology search alignment.*
Lerner Nature 299:592–596 1982.*
Charo, I.F. et al., "Molecular cloning and functional expression of two monocyte chemoattractant protein 1 receptors reveals alternative splicing of the carboxyl–terminal tails," *Proc. Natl. Acad. Sci. USA* 91:2752–2756 (Mar. 1994).
Eva, C. et al., "Molecular cloning of a novel G protein–coupled receptor that may belong to the neuropeptide receptor family," *FEBS Letters* 271:81–84 (1990).
Gao, J.–L. et al., "Structure and Functional Expression of the Human Macrophage Inflammatory Protein 1α/RANTES Receptor," *J. Exp. Med.* 117:1421–1427 (1993).
George, D.G. et al., "Chapter 12. Current Methods in Sequence Comparison and Analysis," in: Macromolecular Sequencing and Synthesis. Selected Methods and Applications, Alan R. Liss, Inc., pp. 127–149 (1988).
Hla, T. and T. Maciang, "An abundant transcript induced in differentiating human endothelial cells encodes a polypeptide with structural similarities to G–protein–coupled receptors," *J. Biol. Chem.* 265:9308–9313 (1990).
Libert, F. et al., "Selective amplification and cloning of four new members of the G protein–coupled receptor family," *Science* 244:569–572 (1989).
Meyerhof, W. et al., "Molecular cloning of a novel putative G–protein coupled receptor expressed during rat spermiogenesis," *FEBS Letters* 284:155–160 (1991).
Neote, K. et al., "Molecular Cloning, Functional Expression, and Signaling Characteristics of a C–C Chemokine Receptor," *Cell* 72:415–425 (1993).
Nomura, H. et al., "Molecular cloning of cDNAs encoding a LD78 receptor and putative leukocyte chemotactic peptide receptors," *Intl. Immunol.* 5:1239–1249 (1993).
Ross, P.C. et al., "RTA, a candidate G protein–coupled receptor: cloning, sequencing, and tissue distribution," *Proc. Natl. Acad. Sci. USA* 87:3052–3056 (1990).
Yamagami, S. et al., "cDNA Cloning and Functional Expression of a Human Monocyte Chemoattractant Protein 1 Receptor," *Biochem. Biophys. Res. Comm.* 202:1156–1162 (Jul. 1994).
NCBI Entrez, Genbank Report, Accession No. M74240, Beckman, M.P. et al. (1991).
NCBI Entrez, Genbank Report, Accession No. L10918, Gao, J.–L. et al. (1993).
NCBI Entrez, Genbank Report, Accession No. U03882, Charo, I.F. et al. (Jun. 1994).
NCBI Entrez, Genbank Report, Accession No. D10925, Nomura, H. et al. (Sep. 1994).
NCBI Entrez, Genbank Report, Accession No. L09230, Neote, K. et al. (Dec. 1994).
NCBI Entrez, Genbank Report, Accession No. L24445, Prado, G.N. et al. (May 1994).
NCBI Entrez, Genbank Report, Accession No. U29677, Post, T.W. et al. (1996).
NCBI Entrez, Genbank Report, Accession No. U28406, Gao, J.L. and Murphy, P.M. (1996).
NCBI Entrez, Genbank Report, Accession No. D29984, Yamagami, S. et al. (1996).
NCBI Entrez, Genbank Report, Accession No. U47036, Boring, L. et al. (1996).
NCBI Entrez, Genbank Report, Accession No. U47035, Boring, L. et al. (1996).
NCBI Entrez, Genbank Report, Accession No. U28694, Combadiere, C. et al. (1996).
NCBI Entrez, Genbank Report, Accession No. U51717, Kurihara, T. and Bravo, R. (1996).

NCBI Entrez, Genbank Report, Accession No. X94151, Meyer, A. et al. (1996).
NCBI Entrez, Genbank Report, Accession No. U54994, Raport, C.J. et al. (1996).
NCBI Entrez, Genbank Report, Accession No. X99393, Samson, M. et al. (1996).
NCBI Entrez, Genbank Report, Accession No. U56819, Heesen, M. et al. (1996).
NCBI Entrez, Genbank Report, Accession No. U49727, Ponath, P.D. et al. (1996).
NCBI Entrez, Genbank Report, Accession No. X91492, Samson, M. et al. (1996).
NCBI Entrez, Genbank Report, Accession No. U51241, Daugherty, B.L. (1996).
NCBI Entrez, Genbank Report, Accession No. U57840, Combadiere, C. et al. (1996).
NCBI Entrez, Genbank Report, Accession No. U68565, Kuziel, W.A. and Maeda, N. (1996).
NCBI Entrez, Genbank Report, Accession No. U70988, Dunstan, C.A.N. et al. (1996).
Alkhatib, G. et al., "CC CKR5: A Rantes, MIP–1α, MIP–1β Receptor as a Fusion Cofactor for Macrophage–Tropic HIV–1," *Science* 272:1955–1958 (Jun. 1996).
Balter, M., "Elusive HIV–Suppressor Factors Found," *Science* 270:1560–1561 (Dec. 1995).
Balter, M., "A Second Coreceptor for HIV In Early Stages of Infection," *Science* 272:1740 (Jun. 1996).
Choe, H. et al., "The β–Chemokine Receptors CCR3 and CCR5 Facilitate Infection by Primary HIV–1 Isolates," *Cell* 85:1135–1148 (Jun. 1996).
Cocchi, F. et al., "Identification of RANTES, MIP–1α, and MIP–1β as the Major HIV–Suppressive Factors Produced by CD8+ T Cells," *Science* 270:1811–1815 (Dec. 1995).
Cohen, J., "Likely HIV Cofactor Found," *Science* 272:809–810 (May 1996).
Combadiere, C. et al., "Cloning and functional expression of a human eosinophil CC chemokine receptor," *J. Biol. Chem.* 270:16491–16494 (Jul. 1995).
Combadiere, C. et al., "Monocyte Chemoattractant Protein–3 Is a Functional Ligand for CC Chemokine Receptors 1 and 2," *J. Biol. Chem.* 270:29671–29675 (Dec. 1995).
Combadiere, C. et al., "Additions and Corrections to: Cloning and functional expression of a human eosinophil CC chemokine receptor," *J. Biol. Chem.* 270:30235 (Dec. 1995).
Combadiere, C. et al., "Cloning and functional expression of CC CKR5, a human monocyte CC chemokine receptor selective for MIP–1α, MIP–1β, and RANTES," *J. Leukocyte Biol.* 60:147–152 (Jul. 1996).
Deng, H. et al., "Identification of a major co–receptor for primary isolates of HIV–1," *Nature* 381:661–666 (Jun. 1996).
Dimitrov, D.S., "Fusion—a place for HIV–1 and T4 cells to meet," *Nature Med.* 2:640–641 (Jun. 1996).
Doranz, B.J. et al., "A Dual–Tropic Primary HIV–1 Isolate That Uses Fusin and the β–Chemkine Receptors CKR–5, CKR–3, and CKR–2b as Fusion Cofactors," *Cell* 85:1149–1158 (Jun. 1996).
Dragic, T. et al., "HIV–1 entry into CD4+ cells is mediated by the chemokine receptor CC–CKR–5," *Nature* 381:667–673 (Jun. 1996).
Feng, Y. et al., "HIV–1 Entry Cofactor: Functional cDNA Cloning of a Seven–Transmembrane, G Protein–Coupled Receptor," *Science* 272:872–877 (May 1996).

Gura, T., "Chemokines Take Center Stage in Inflammatory Ills," *Science* 272:954–956 (May 1996).
Marshall, E., "HIV Experts vs. Sequencers in Patent Race," *Science* 275:1263 (Feb. 1997).
Murphy, P.M., "The Molecular Biology of Leukocyte Chemoattractant Receptors," *Annu. Rev. Immunol.* 12:593–633 (1994).
Raport, C.J. et al., "Molecular Cloning and Functional Characterization of a Novel Human CC Chemokine Receptor (CCR5) for RANTES, MIP–1β, and MIP–1α," *J. Biol. Chem.* 271:17161–17166 (Jul. 1996).
Samson, M. et al., "Molecular Cloning and Functional Expression of a New Human CC–Chemokine Receptor Gene," *Chem. Abstracts* 124:993, Abstract No. 258056e (May 1996).
Samson, M. et al., "Molecular Cloning and Functional Expression of a New Human CC–Chemokine Receptor Gene," *Biochem.* 35:3362–3367 (Mar. 1996).
Travis, J., "Multiple doors for HIV to enter cells," *Science News* 149:390 (Jun. 1996).
Weiss, R.A. and P.R. Clapham, "Hot fusion of HIV," *Nature* 381:647–648 (Jun. 1996).
Dialog, File 351 (Derwent), English language abstract of EP 0 671 391.
Dialog, File 351 (Derwent), English language abstract of EP 0 612 723.
Dialog, File 351 (Derwent), English language abstract of FR 2 771 423.
Dialog, File 351 (Derwent), English language abstract of JP 11–243960.
Dialog, File 351 (Derwent), English language abstract of JP 11–292795.
Dialog, File 351 (Derwent), English language abstract of EP 0 979 655.
Lee, N.H., "Molecular Biology of G–Protein–Coupled Receptors," *DN & P* 6:488–497 (1993).
Oliveira, L. et al., "A common motif in G–protein–coupled seven transmembrane helix receptors," *J. Computer–Aided Molecular Design* 7:649–658 (1993).
Probst, W.C. et al., "Sequence Alignment of the G–Protein Coupled Receptor Superfamily," *DNA and Cell Biol.* 11:1–20 (1992).
Dialog, File 351 (Derwent), English language abstract of RU 2126048.
Cunningham, M.W., et al., "Cytotoxic and viral neutralizing antibodies crossreact with streptococcal M protein, enteroviruses, and human cardiac myosin," *Proc. Natl. Acad. Sci. USA* 89:1320–1324, National Academy of Science of the USA (1992).
Genbank Accession No. AF019772, Peiper, S.C. and Lu, Z.–H., "Mus musculus CCR5 gene," (1997).
Bendig, M.M., "Humanization of Rodent Monoclonal Antibodies by CDR Grafting," *Methods* 8:83–93 (Oct. 1995) (Academic Press, Inc.).
Horuk, R., "Molecular properties of the chemokine receptor family," *Trends Pharmacol. Sci.* 15:159–165 (May 1994) (Elsevier Science Ltd).
Lee, B., et al., "Epitope Mapping of CCR5 Reveals Multiple Conformational States and Distinct but Overlapping Structures Involved in Chemokine and Coreceptor Function," *J. Biol. Chem.* 274:9617–9626 (Apr. 1999) (American Society for Biochemistry and Molecular Biology).

Olson, W.C., et al., "Differential Inhibition of Human Immunodeficiency Virus Type 1 Fusion, gp120 Binding, and CC–Chemokine Activity by Monoclonal Antibodies to CCR5," *J. Virol.* 73:4145–4155 (May 1999) (American Society for Microbiology).

Osbourn, J.K., et al., "Directed selection of MIP–1α neutralizing CCR5 antibodies from a phage display human antibody library," *Nature Biotechnol.* 16:778–781 (Aug. 1998) (Nature Publishing Group).

Probst, W.C., et al., "Sequence Alignment of the G–Protein Coupled Receptor Superfamily," *DNA and Cell Biology* 11:1–20 (1992) (Mary Ann Liebert, Inc.).

Schall, T.J., "Biology of the RANTES/SIS Cytokine Family," *Cytokine* 3:165–183 (1991) (Academic Press).

Wu, L., et al., "Interaction of Chemokine Receptor CCR5 with its Ligands: Multiple Domains for HIV–1 gp120 Binding and a Single Domain for Chemokine Binding," *J. Exp. Med.* 186:1373–1381 (Oct. 1997) (The Rockefeller University Press).

U.S. patent application Publication No. US–2002–0061834–A1, Li et al., May 23, 2002.

Burbach, J.P.H., and Meijer, O.C., "The Structure of Neuropeptide Receptors," *Eur. J. Pharmacol.—Mol. Pharmacol. Sect.* 227:1–18, Elsevier Science Publishers B.V. (1992).

Greenwood, M.T. et al., "Ligand Binding Pocket of the Human Somatostatin Receptor 5: Mutational Analysis of the Extracellular Domains," *Mol. Pharmacol.* 52:807–814, The American Society for Pharmacology and Experimental Therapeutics (1997).

Larhammar, D. et al., "The Receptor Revolution—Multiplicity of G–Protein–Coupled Receptors," *Drug Design Discovery* 9:179–188, Harwood Academic Publishers GmbH (1993).

* cited by examiner

```
  1 GTGAGATGGT GCTTTCATGA ATTCCCCCAA CAAGAGCCAA GCTCTCCATC  50

51 TAGTGGACAG GGAAGCTAGC AGCAAACCTT CCCTTCACTA CGAAACTTCA 100

101 TTGCTTGGCC CAAAAGAGAG TTAATTCAAT GTAGACATCT ATGTAGGCAA 150

151 TTAAAAACCT ATTGATGTAT AAAACAGTTT GCATTCATGG AGGGCAACTA 200

201 AATACATTCT AGGACTTTAT AAAAGATCAC TTTTTATTTA TGCACAGGGT 250

251 GGAACAAGAT GGATTATCAA GTGTCAAGTC CAATCTATGA CATCAATTAT 300
             M   D  Y  Q   V  S  S   P  I  Y   D  I  N  Y

301 TATACATCGG AGCCCTGCCA AAAAATCAAT GTGAAGCAAA TCGCAGCCCG 350
     Y  T  S   E  P  C   Q  K  I  N   V  K  Q   I  A  A  R

351 CCTCCTGCCT CCGCTCTACT CACTGGTGTT CATCTTTGGT TTTGTGGGCA 400
     L  L  P   P  L  Y   S  L  V  F   I  F  G   F  V  G

401 ACATGCTGGT CATCCTCATC CTGATAAACT GCAAAAGGCT GAAGAGCATG 450
     N  M  L   V  I  L   I  L  I  N   C  K  R   L  K  S  M

451 ACTGACATCT ACCTGCTCAA CCTGGCCATC TCTGACCTGT TTTTCCTTCT 500
     T  D  I   Y  L  L   N  L  A  I   S  D  L   F  F  L  L

501 TACTGTCCCC TTCTGGGCTC ACTATGCTGC CGCCCAGTGG GACTTTGGAA 550
     T  V  P   F  W  A   H  Y  A  A   A  Q  W   D  F  G

551 ATACAATGTG TCAACTCTTG ACAGGGCTCT ATTTTATAGG CTTCTTCTCT 600
     N  T  M  C   Q  L  L   T  G  L   Y  F  I  G   F  F  S

601 GGAATCTTCT TCATCATCCT CCTGACAATC GATAGGTACC TGGCTGTCGT 650
     G  I  F   F  I  I  L   L  T  I   D  R  Y   L  A  V  V
```

FIG. 1A

```
651 CCATGCTGTG TTTGCTTTAA AAGCCAGGAC GGTCACCTTT GGGGTGGTGA 700
     H  A  V  F  A  L  K  A  R  T  V  T  F  G  V  V

701 CAAGTGTGAT CACTTGGGTG GTGGCTGTGT TTGCGTCTCT CCCAGGAATC 750
     T  S  V  I  T  W  V  V  A  V  F  A  S  L  P  G  I

751 ATCTTTACCA GATCTCAAAA AGAAGGTCTT CATTACACCT GCAGCTCTCA 800
      I  F  T  R  S  Q  K  E  G  L  H  Y  T  C  S  S  H

801 TTTTCCATAC AGTCAGTATC AATTCTGGAA GAATTTCCAG ACATTAAAGA 850
      F  P  Y  S  Q  Y  Q  F  W  K  N  F  Q  T  L  K

851 TAGTCATCTT GGGGCTGGTC CTGCCGCTGC TTGTCATGGT CATCTGCTAC 900
      I  V  I  L  G  L  V  L  P  L  L  V  M  V  I  C  Y

901 TCGGGAATCC TAAAAACTCT GCTTCGGTGT CGAAATGAGA AGAAGAGGCA 950
      S  G  I  L  K  T  L  L  R  C  R  N  E  K  K  R  H

951 CAGGGCTGTG AGGCTTATCT TCACCATCAT GATTGTTTAT TTTCTCTTCT 1000
      R  A  V  R  L  I  F  T  I  M  I  V  Y  F  L  F

1001 GGGCTCCCTA CAACATTGTC CTTCTCCTGA ACACCTTCCA GGAATTCTTT 1050
      W  A  P  Y  N  I  V  L  L  L  N  T  F  Q  E  F  F

1051 GGCCTGAATA ATTGCAGTAG CTCTAACAGG TTGGACCAAG CTATGCAGGT 1100
      G  L  N  N  C  S  S  S  N  R  L  D  Q  A  M  Q  V

1101 GACAGAGACT CTTGGGATGA CGCACTGCTG CATCAACCCC ATCATCTATG 1150
      T  E  T  L  G  M  T  H  C  C  I  N  P  I  I  Y

1151 CCTTTGTCGG GGAGAAGTTC AGAAACTACC TCTTAGTCTT CTTCCAAAAG 1200
      A  F  V  G  E  K  F  R  N  Y  L  L  V  F  F  Q  K
```

FIG. 1B

```
1201 CACATTGCCA AACGCTTCTG CAAATGCTGT TCTATTTTCC AGCAAGAGGC 1250
      H  I  A   K  R  F   C  K  C   S  I  F    Q  Q  E  A

1251 TCCCGAGCGA GCAAGCTCAG TTTACACCCG ATCCACTGAG GAGCAGGAAA 1300
      P  E  R   A  S  S   V  Y  T  R  S  T  E   E  Q  E

1301 TATCTGTGGG CTTGTGACAC GGACTCAAGT GGGCTGGTGA CCCAGTCAGA 1350
      I  S  V  G   L  *

1351 GTTGTGCACA TGGCTTAGTT TTCATACACA GCCTGGGCTG GGGGTGGGGT 1400

1401 GGAAGAGGTC TTTT 1414
```

FIG. 1C

```
  4 QVSSPIYDINYYTSEPCQKINVKQIAARLLPPLYSLVFIFGFVGNMLVIL  53
    :  ..::|.:|  :.||.|::||||:|.|||||||||||||||||:|
 18 EEVTTFFDYDY..GAPCHKFDVKQIGAQLLPPLYSLVFIFGFVGNMLVVL  65

54 ILINCKRLKSMTDIYLLNLAISDLFFLLTVPFWAHYAAAQWDFGNTMCQL 103
    |||||.:|.::|||||||||||:||:|:|:||| ||.:| |||.||.|
 66 ILINCKKLKCLTDIYLLNLAISDLLFLITLPLWAHSAANEWVFGNAMCKL 115

104 LTGLYFIGFFSGIFFIILLTIDRYLAVVHAVFALKARTVTFGVVTSVITW 153
    :|||| ||:|:|||||||||||||||||||||||||||||||||||||||
116 FTGLYHIGYFGGIFFIILLTIDRYLAIVHAVFALKARTVTFGVVTSVITW 165

154 VVAVFASLPGIIFTRSQKEGLHYTCSSHFPYSQYQFWKNFQTLKIVILGL 203
    :||||||:||||||::|||: |.|...|| : |.||:|:. ||||
166 LVAVFASVPGIIFTKCQKEDSVYVCGPYFPRG....WNNFHTIMRNILGL 211

204 VLPLLVMVICYSGILKTLLRCRNEKKRHRAVRLIFTIMIVYFLFWAPYNI 253
    ||||:|||||||||||||||||||||||||||:||||||||||.||||
212 VLPLLIMVICYSGILKTLLRCRNEKKRHRAVRVIFTIMIVYFLFWTPYNI 261

254 VLLLNTFQEFFGLNNCSSSNRLDQAMQVTETLGMTHCCINPIIYAFVGEK 303
    |:||||||||.||.|...|||| ||||||||||||||||||||||||||
262 VILLNTFQEFFGLSNCESTSQLDQATQVTETLGMTHCCINPIIYAFVGEK 311

304 FRNYLLVFFQKHIAKRFCKCCSIFQQEAPERASSVYTRS...TEEQEISV 350
    ||..: :.:||  .: |...:  .. |::..| |.:  . ..: |:
312 FRSLFHIALGCRIA.PLQKPVCGGPGVRPGKNVKVTTQGLLDGRGKGKSI 360

ANTIBODIES TO HUMAN G-PROTEIN CHEMOKINE RECEPTOR HDGNR10 (CCR5RECEPTOR)

The present application is a divisional of U.S. application Ser. No 08/466,343, filed Jun. 6, 1995, U.S. Pat. No. 6,025,154, which disclosure is herein incorporated by reference.

This invention relates to newly identified polynucleotides, polypeptides encoded by such polynucleotides, the use of such polynucleotides and polypeptides, as well as the production of such polynucleotides and polypeptides. More particularly, the polypeptide of the present invention is a human 7-transmembrane receptor which has been putatively identified as a chemokine receptor, sometimes hereinafter referred to as "G-Protein Chemokine Receptor" or "HDGNR10". The invention also relates to inhibiting the action of such polypeptides.

It is well established that many medically significant biological processes are mediated by proteins participating in signal transduction pathways that involve G-proteins and/or second messengers, e.g., CAMP (Lefkowitz, Nature, 351:353–354 (1991)). Herein these proteins are referred to as proteins participating in pathways with G-proteins or PPG proteins. Some examples of these proteins include the GPC receptors, such as those for adrenergic agents and dopamine (Kobilka, B. K., et al., PNAS, 84:46–50 (1987); Kobilka, B. K., et al., Science, 238:650–656 (1987); Bunzow, J. R., et al., Nature, 336:783–787 (1988)), G-proteins themselves, effector proteins, e.g., phospholipase C, adenyl cyclase, and phosphodiesterase, and actuator proteins, e.g., protein kinase A and protein kinase C (Simon, M. I., et al., Science, 252:802–8 (1991)).

For example, in one form of signal transduction, the effect of hormone binding is activation of an enzyme, adenylate cyclase, inside the cell. Enzyme activation by hormones is dependent on the presence of the nucleotide GTP, and GTP also influences hormone binding. A G-protein connects the hormone receptors to adenylate cyclase. G-protein was shown to exchange GTP for bound GDP when activated by hormone receptors. The GTP-carrying form then binds to an activated adenylate cyclase. Hydrolysis of GTP to GDP, catalyzed by the G-protein itself, returns the G-protein to its basal, inactive form. Thus, the G-protein serves a dual role, as an intermediate that relays the signal from receptor to effector, and as a clock that controls the duration of the signal.

The membrane protein gene superfamily of G-protein coupled receptors has been characterized as having seven putative transmembrane domains. The domains are believed to represent transmembrane α-helices connected by extracellular or cytoplasmic loops. G-protein coupled receptors include a wide range of biologically active receptors, such as hormone, viral, growth factor and neuroreceptors.

G-protein coupled receptors have been characterized as including these seven conserved hydrophobic stretches of about 20 to 30 amino acids, connecting at least eight divergent hydrophilic loops. The G-protein family of coupled receptors includes dopamine receptors which bind to neuroleptic drugs used for treating psychotic and neurological disorders. Other examples of members of this family include calcitonin, adrenergic, endothelin, CAMP, adenosine, muscarinic, acetylcholine, serotonin, histamine, thrombin, kinin, follicle stimulating hormone, opsins, endothelial differentiation gene-1 receptor and rhodopsins, odorant, cytomegalovirus receptors, etc.

G-protein coupled receptors can be intracellularly coupled by heterotrimeric G-proteins to various intracellular enzymes, ion channels and transporters (see, Johnson et al., Endoc., Rev., 10:317–331 (1989)). Different G-protein α-subunits preferentially stimulate particular effectors to modulate various biological functions in a cell. Phosphorylation of cytoplasmic residues of G-protein coupled receptors have been identified as an important mechanism for the regulation of G-protein coupling of some G-protein coupled receptors. G-protein coupled receptors are found in numerous sites within a mammalian host.

Chemokines, also referred to as intercrine cytokines, are a subfamily of structurally and functionally related cytokines. These molecules are 8–10 kd in size. In general, chemokines exhibit 20% to 75% homology at the amino acid level and are characterized by four conserved cysteine residues that form two disulfide bonds. Based on the arrangement of the first two cysteine residues, chemokines have been classified into two subfamilies, alpha and beta. In the alpha subfamily, the first two cysteines are separated by one amino acid and hence are referred to as the "C-X-C" subfamily. In the beta subfamily, the two cysteines are in an adjacent position and are, therefore, referred to as the "C-C" subfamily. Thus far, at least nine different members of this family have been identified in humans.

The intercrine cytokines exhibit a wide variety of functions. A hallmark feature is their ability to elicit chemotactic migration of distinct cell types, including monocytes, neutrophils, T lymphocytes, basophils and fibroblasts. Many chemokines have proinflammatory activity and are involved in multiple steps during an inflammatory reaction. These activities include stimulation of histamine release, lysosomal enzyme and leukotriene release, increased adherence of target immune cells to endothelial cells, enhanced binding of complement proteins, induced expression of granulocyte adhesion molecules and complement receptors, and respiratory burst. In addition to their involvement in inflammation, certain chemokines have been shown to exhibit other activities. For example, macrophage inflammatory protein 1 (MIP-1) is able to suppress hematopoietic stem cell proliferation, platelet factor-4 (PF-4) is a potent inhibitor of endothelial cell growth, Interleukin-8 (IL-8) promotes proliferation of keratinocytes, and GRO is an autocrine growth factor for melanoma cells.

In light of the diverse biological activities, it is not surprising that chemokines have been implicated in a number of physiological and disease conditions, including lymphocyte trafficking, wound healing, hematopoietic regulation and immunological disorders such as allergy, asthma and arthritis.

In accordance with one aspect of the present invention, there are provided novel mature receptor polypeptides as well as biologically active and diagnostically or therapeutically useful fragments, analogs and derivatives thereof. The receptor polypeptides of the present invention are of human origin.

In accordance with another aspect of the present invention, there are provided isolated nucleic acid molecules encoding the receptor polypeptides of the present invention, including mRNAs, DNAS, cDNAs, genomic DNA as well as antisense analogs thereof and biologically active and diagnostically or therapeutically useful fragments thereof.

In accordance with a further aspect of the present invention, there are provided processes for producing such receptor polypeptides by recombinant techniques comprising culturing recombinant prokaryotic and/or eukaryotic host cells, containing nucleic acid sequences encoding the receptor polypeptides of the present invention, under conditions promoting expression of said polypeptides and subsequent recovery of said polypeptides.

In accordance with yet a further aspect of the present invention, there are provided antibodies against such receptor polypeptides.

In accordance with another aspect of the present invention there are provided methods of screening for compounds which bind to and activate or inhibit activation of the receptor polypeptides of the present invention.

In accordance with still another embodiment of the present invention there are provided processes of administering compounds to a host which bind to and activate the receptor polypeptide of the present invention which are useful in stimulating haematopoiesis, wound healing, coagulation, angiogenesis, to treat solid tumors, chronic infections, leukemia, T-cell mediated auto-immune diseases, parasitic infections, psoriasis, and to stimulate growth factor activity.

In accordance with another aspect of the present invention there is provided a method of administering the receptor polypeptides of the present invention via gene therapy to treat conditions related to underexpression of the polypeptides or underexpression of a ligand for the receptor polypeptide.

In accordance with still another embodiment of the present invention there are provided processes of administering compounds to a host which bind to and inhibit activation of the receptor polypeptides of the present invention which are useful in the prevention and/or treatment of allergy, atherogenesis, anaphylaxis, malignancy, chronic and acute inflammation, histamine and IgE-mediated allergic reactions, prostaglandin-independent fever, bone marrow failure, silicosis, sarcoidosis, rheumatoid arthritis, shock and hyper-eosinophilic syndrome.

In accordance with yet another aspect of the present invention, there are provided nucleic acid probes comprising nucleic acid molecules of sufficient length to specifically hybridize to the polynucleotide sequences of the present invention.

In accordance with still another aspect of the present invention, there are provided diagnostic assays for detecting diseases related to mutations in the nucleic acid sequences encoding such polypeptides and for detecting an altered level of the soluble form of the receptor polypeptides.

In accordance with yet a further aspect of the present invention, there are provided processes for utilizing such receptor polypeptides, or polynucleotides encoding such polypeptides, for in vitro purposes related to scientific research, synthesis of DNA and manufacture of DNA vectors.

These and other aspects of the present invention should be apparent to those skilled in the art from the teachings herein.

BRIEF DESCRIPTION OF THE DRAWING

The following drawings are illustrative of embodiments of the invention and are not meant to limit the scope of the invention as encompassed by the claims.

FIGS. 1A–1C show the DNA sequence and the corresponding deduced amino acid sequence of the G-protein coupled receptor of the present invention. The standard one-letter abbreviation for amino acids is used. Sequencing was performed using a 373 Automated DNA sequencer (Applied Biosystems, Inc.).

FIG. 2 illustrates an amino acid sequence alignment utilizing the standard one-letter code amino acid representation of the G-protein coupled chemokine receptor of the present invention (portions of SEQ ID NO:2) and a comparative portion (SEQ ID NO:9) of the amino acid sequence for the human MCP-1 receptor protein.

DETAILED DESCRIPTION OF THE INVENTION

In accordance with an aspect of the present invention, there is provided an isolated nucleic acid (polynucleotide) which encodes for the mature polypeptide having the deduced amino acid sequence of FIGS. 1A–1C (SEQ ID NO:2) or for the mature polypeptide encoded by the clone deposited as ATCC Deposit No. 97183 on Jun. 1, 1995 at the American Type Culture Collection, Patent Depository, 10801 University Boulevard, Manassas, Va. 20110-2209.

The polynucleotide of this invention was discovered in human genomic library. It is structurally related to the G protein-coupled receptor family. It contains an open reading frame encoding a protein of 352 amino acid residues. The protein exhibits the highest degree of homology to a human MCP-1 receptor with 70.1% identity and 82.9% similarity over a 347 amino acid stretch.

The polynucleotide of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The coding sequence which encodes the mature polypeptide may be identical to the coding sequence shown in FIGS. 1A–1C (SEQ ID NO:1) or that of the deposited clone or may be a different coding sequence which coding sequence, as a result of the redundancy or degeneracy of the genetic code, encodes the same mature polypeptide as the DNA of FIGS. 1A–1C (SEQ ID NO:1) or the deposited clone.

The polynuleotide which encodes for the mature polypeptide of FIGS. 1A–1C or for the mature polypeptide encoded by the deposited clone may include: only the coding sequence for the mature polypeptide; the coding sequence for the mature polypeptide and additional coding sequence such as a transmembrane (TM) or intra-cellular domain; the coding sequence for the mature polypeptide (and optionally additional coding sequence) and non-coding sequence, such as introns or non-coding sequence 5' and/or 3' of the coding sequence for the mature polypeptide.

Thus, the term "polynucleotide encoding a polypeptide" encompasses a polynucleotide which includes only coding sequence for the polypeptide as well as a polynucleotide which includes additional coding and/or non-coding sequence.

The present invention further relates to variants of the hereinabove described polynucleotides which encode for fragments, analogs and derivatives of the polypeptide having the deduced amino acid sequence of FIGS. 1A–1C or the polypeptide encoded by the deposited clone. The variant of the polynucleotide may be a naturally occurring allelic variant of the polynucleotide or a non-naturally occurring variant of the polynucleotide.

Thus, the present invention includes polynucleotides encoding the same mature polypeptide as shown in FIGS. 1A–1C (SEQ ID NO:2) or the same mature polypeptide encoded by the deposited clone as well as variants of such polynucleotides which variants encode for a fragment, derivative or analog of the polypeptide of FIGS. 1A–1C (SEQ ID NO:2) or the polypeptide encoded by the the deposited clone. Such nucleotide variants include deletion variants, substitution variants and addition or insertion variants.

As hereinabove indicated, the polynucleotide may have a coding sequence which is a naturally occurring allelic variant of the coding sequence shown in FIGS. 1A–1C SEQ ID NO:1) or of the coding sequence of the deposited clone. As known in the art, an allelic variant is an alternate form of a polynucleotide sequence which may have a substitution, deletion or addition of one or more nucleotides, which does not substantially alter the function of the encoded polypeptide.

The polynucleotides may also encode for a soluble form of the G-protein chemokine receptor polypeptide which is the extracellular portion of the polypeptide which has been cleaved from the TM and intracellular domain of the full-length polypeptide of the present invention.

The polynucleotides of the present invention may also have the coding sequence fused in frame to a marker sequence which allows for purification of the polypeptide of the present invention. The marker sequence may be a hexa-histidine tag supplied by a pQE-9 vector to provide for purification of the mature polypeptide fused to the marker in the case of a bacterial host, or, for example, the marker sequence may be a hemagglutinin (HA) tag when mammalian host, e.g. COS-7 cells, is used. The HA tag corresponds to an epitope derived from the influenza hemagglutinin protein (Wilson, I., et al., Cell, 37:767 (1984)).

The term "gene" means the segment of DNA involved in producing a polypeptide chain; it includes regions preceding and following the coding region (leader and trailer) as well as intervening sequences (introns) between individual coding segments (exons).

Fragments of the full length gene of the present invention may be used as a hybridization probe for a cDNA library to isolate the full length cDNA and to isolate other cDNAs which have a high sequence similarity to the gene or similar biological activity. Probes of this type preferably have at least 30 bases and may contain, for example, 50 or more bases. The probe may also be used to identify a cDNA clone corresponding to a full length transcript and a genomic clone or clones that contain the complete gene including regulatory and promotor regions, exons, and introns. An example of a screen comprises isolating the coding region of the gene by using the known DNA sequence to synthesize an oligonucleotide probe. Labeled oligonucleotides having a sequence complementary to that of the gene of the present invention are used to screen a library of human cDNA, genomic DNA or mRNA to determine which members of the library the probe hybridizes to.

The present invention further relates to polynucleotides which hybridize to the hereinabove-described sequences if there is at least 70%, preferably at least 90%, and more preferably at least 95% identity between the sequences. The present invention particularly relates to polynucleotides which hybridize under stringent conditions to the hereinabove-described polynucleotides. As herein used, the term "stringent conditions" means hybridization will occur only if there is at least 95% and preferably at least 97% identity between the sequences. The polynucleotides which hybridize to the hereinabove described polynucleotides in a preferred embodiment encode polypeptides which either retain substantially the same biological function or activity boas the mature polypeptide encoded by the DNA of FIGS. 1A–1C (SEQ ID NO:1) or the deposited clone.

Alternatively, the polynucleotide may have at least 20 bases, preferably 30 bases, and more preferably at least 50 bases which hybridize to a polynucleotide of the present invention and which has an identity thereto, as hereinabove described, and which may or may not retain activity. For example, such polynucleotides may be employed as probes for the polynucleotide of SEQ ID NO:1, for example, for recovery of the polynucleotide or as a diagnostic probe or as a PCR primer.

Thus, the present invention is directed to polynucleotides having at least a 70% identity, preferably at least 90% and more preferably at least a 95% identity to a polynucleotide which encodes the polypeptide of SEQ ID NO:2 as well as fragments thereof, which fragments have at least 30 bases and preferably at least 50 bases and to polypeptides encoded by such polynucleotides.

The deposit(s) referred to herein will be maintained under the terms of the Budapest Treaty on the International Recognition of the Deposit of Micro-organisms for purposes of Patent Procedure. These deposits are provided merely as convenience to those of skill in the art and are not an admission that a deposit is required under 35 U.S.C. §112. The sequence of the polynucleotides contained in the deposited materials, as well as the amino acid sequence of the polypeptides encoded thereby, are incorporated herein by reference and are controlling in the event of any conflict with any description of sequences herein. A license may be required to make, or sell the deposited materials, and no such license is hereby granted.

The present invention further relates to a G-protein chemokine receptor polypeptide which has the deduced amino acid sequence of FIGS. 1A–1C (SEQ ID NO:2) or which has the amino acid sequence encoded by the deposited clone, as well as fragments, analogs and derivatives of such polypeptide.

The terms "fragment," "derivative and "analog" when referring to the polypeptide of FIGS. 1A–1C or that encoded by the deposited clone, means a polypeptide which either retains substantially the same biological function or activity as such polypeptide, i.e. functions as a G-protein chemokine receptor, or retains the ability to bind the ligand or the receptor even though the polypeptide does not function as a G-protein chemokine receptor, for example, a soluble form of the receptor. An analog includes a proprotein which can be activated by cleavage of the proprotein portion to produce an active mature polypeptide.

The polypeptide of the present invention may be a recombinant polypeptide, a natural polypeptide or a synthetic polypeptide, preferably a recombinant polypeptide.

The fragment, derivative or analog of the polypeptide of FIGS. 1A–1C (SEQ ID NO:2) or that encoded by the deposited clone may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide for purification of the polypeptide or (v) one in which a fragment of the polypeptide is soluble, i.e. not membrane bound, yet still binds ligands to the membrane bound receptor. Such fragments, derivatives and analogs are deemed to be within the scope of those skilled in the art from the teachings herein.

The polypeptides and polynucleotides of the present invention are preferably provided in an isolated form, and preferably are purified to homogeneity.

The polypeptides of the present invention include the polypeptide of SEQ ID NO:2 (in particular the mature polypeptide) as well as polypeptides which have at least 70% similarity (preferably a 70% identity) to the polypeptide of SEQ ID NO:2 and more preferably a 90% similarity (more preferably a 90% identity) to the polypeptide of SEQ ID NO:2 and still more preferably a 95% similarity (still more preferably a 90% identity) to the polypeptide of SEQ ID NO:2 and to portions of such polypeptide with such portion of the polypeptide generally containing at least 30 amino acids and more preferably at least 50 amino acids.

As known in the art "similarity" between two polypeptides is determined by comparing the amino acid sequence and conserved amino acid substitutes thereto of the polypeptide to the sequence of a second polypeptide.

Fragments or portions of the polypeptides of the present invention may be employed for producing the corresponding full-length polypeptide by peptide synthesis, therefore, the fragments may be employed as intermediates for producing the full-length polypeptides. Fragments or portions of the polynucleotides of the present invention may be used to synthesize full-length polynucleotides of the present invention.

The term "gene" means the segment of DNA involved in producing a polypeptide chain; it includes regions preceding and following the coding region "leader and trailer" as well as intervening sequences (introns) between individual coding segments (exons).

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The polypeptides of the present invention include the polypeptide of SEQ ID NO:2 (in particular the mature polypeptide) as well as polypeptides which have at least 70% similarity (preferably at least 70% identity) to the polypeptide of SEQ ID NO:2 and more preferably at least 90% similarity (more preferably at least 90% identity) to the polypeptide of SEQ ID NO:2 and still more preferably at least 95% similarity (still more preferably at least 95% identity) to the polypeptide of SEQ ID NO:2 and also include portions of such polypeptides with such portion of the polypeptide generally containing at least 30 amino acids and more preferably at least 50 amino acids.

As known in the art "similarity" between two polypeptides is determined by comparing the amino acid sequence and its conserved amino acid substitutes of one polypeptide to the sequence of a second polypeptide.

Fragments or portions of the polypeptides of the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention.

The present invention also relates to vectors which include polynucleotides of the present invention, host cells which are genetically engineered with vectors of the invention and the production of polypeptides of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the genes of the present invention. The culture conditions, such as temperature, pH and the like, are those previously used with the host cell selected for expression, and will be apparent to the ordinarily skilled artisan.

The polynucleotides of the present invention may be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in, the expression vector is operatively linked to an appropriate expression control sequence (s) (promoter) to direct mRNA synthesis. As representative examples of such promoters, there may be mentioned: LTR or SV40 promoter, the E. coli. lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic a cell culture, or such as tetracycline or ampicillin resistance in E. coli.

The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as E. coli, Streptomyces, Salmonella typhimurium; fungal cells, such as yeast; insect cells such as Drosophila and Spodoptera Sf9; animal cells such as CHO, COS or Bowes melanoma; adenovirus; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example. Bacterial: pQE70, pQE60, pQE-9 (Qiagen), pbs, pD10, phagescript, psiX174, pbluescript SK, pbsks, pNH8A, pNH16a, PNH18A, pNH46A (Stratagene); ptrc99a, pKK223-3, pKK233-3, pDR540, pRIT5 (Pharmacia). Eukaryotic: pWLNEO, pSV2CAT, pOG44, pXT1, pSG (Stratagene) pSVK3, PBPV, pMSG, pSVL (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are PKK232-8 and PCM7. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation. (Davis, L., Dibner, M., Battey, I., Basic Methods in Molecular Biology, (1986)).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989), the disclosure of which is hereby incorporated by reference.

Transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Examples including the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of E. coli and S. cervisiae TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include E. coli, Bacillus subtilis, Salmonella typhimurium and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well know to those skilled in the art.

Various mammalian cell culture systems can also be employed to express recombinant protein. Examples of mammalian expression systems include the COS-7 lines of monkey kidney fibroblasts, described by Gluzman, Cell, 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The G-protein chemokine receptor polypeptides can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps.

The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated or may be non-glycosylated. Polypeptides of the invention may also include an initial methionine amino acid residue.

The polynucleotides and polypeptides of the present invention may be employed as research reagents and materials for discovery of treatments and diagnostics to human disease.

The G-protein chemokine receptors of the present invention may be employed in a process for screening for compounds which activate (agonists) or inhibit activation (antagonists) of the receptor polypeptide of the present invention.

In general, such screening procedures involve providing appropriate cells which express the receptor polypeptide of the present invention on the surface thereof. Such cells include cells from mammals, yeast, drosophila or E. Coli. In particular, a polynucleotide encoding the receptor of the present invention is employed to transfect cells to thereby express the G-protein chemokine receptor. The expressed receptor is then contacted with a test compound to observe binding, stimulation or inhibition of a functional response.

One such screening procedure involves the use of melanophores which are transfected to express the G-protein chemokine receptor of the present invention. Such a screening technique is described in PCT WO 92/01810 published Feb. 6, 1992.

Thus, for example, such assay may be employed for screening for a compound which inhibits activation of the receptor polypeptide of the present invention by contacting the melanophore cells which encode the receptor with both the receptor ligand and a compound to be screened. Inhibition of the signal generated by the ligand indicates that a compound is a potential antagonist for the receptor, i.e., inhibits activation of the receptor.

The screen may be employed for determining a compound which activates the receptor by contacting such cells with compounds to be screened and determining whether such compound generates a signal, i.e., activates the receptor.

Other screening techniques include the use of cells which express the G-protein chemokine receptor (for example, transfected CHO cells) in a system which measures extracellular pH changes caused by receptor activation, for example, as described in Science, volume 246, pages 181–296 (October 1989). For example, compounds may be contacted with a cell which expresses the receptor polypeptide of the present invention and a second messenger response, e.g. signal transduction or pH changes, may be measured to determine whether the potential compound activates or inhibits the receptor.

Another such screening technique involves introducing RNA encoding the G-protein chemokine receptor into Xenopus oocytes to transiently express the receptor. The receptor oocytes may then be contacted with the receptor ligand and a compound to be screened, followed by detection of inhibition or activation of a calcium signal in the case of screening for compounds which are thought to inhibit activation of the receptor.

Another screening technique involves expressing the G-protein chemokine receptor in which the receptor is linked to a phospholipase C or D. As representative examples of such cells, there may be mentioned endothelial cells, smooth muscle cells, embryonic kidney cells, etc. The screening may be accomplished as hereinabove described by detecting activation of the receptor or inhibition of activation of the receptor from the phospholipase second signal.

Another method involves screening for compounds which inhibit activation of the receptor polypeptide of the present invention antagonists by determining inhibition of binding of labeled ligand to cells which have the receptor on the surface thereof. Such a method involves transfecting a eukaryotic cell with DNA encoding the G-protein chemokine receptor such that the cell expresses the receptor on its surface and contacting the cell with a compound in the presence of a labeled form of a known ligand. The ligand can be labeled, e.g., by radioactivity. The amount of labeled ligand bound to the receptors is measured, e.g., by measuring radioactivity of the receptors. If the compound binds to the receptor as determined by a reduction of labeled ligand which binds to the receptors, the binding of labeled ligand to the receptor is inhibited.

An antibody may antagonize a G-protein chemokine receptor of the present invention, or in some cases an oligopeptide, which bind to the G-protein chemokine receptor but does not elicit a second messenger response such that the activity of the G-protein chemokine receptors is prevented. Antibodies include anti-idiotypic antibodies which recognize unique determinants generally associated with the antigen-binding site of an antibody. Potential antagonist compounds also include proteins which are closely related to the ligand of the G-protein chemokine receptors, i.e. a fragment of the ligand, which have lost biological function and when binding to the G-protein chemokine receptor elicit no response.

An antisense construct prepared through the use of antisense technology, may be used to control gene expression through triple-helix formation or antisense DNA or RNA, both of which methods are based on binding of a polynucleotide to DNA or RNA. For example, the 5' coding portion of the polynucleotide sequence, which encodes for the mature polypeptides of the present invention, is used to design an antisense RNA oligonucleotide of from about 10 to 40 base pairs in length. A DNA oligonucleotide is designed to be complementary to a region of the gene involved in transcription (triple helix —see Lee et al., Nucl. Acids Res., 6:3073 (1979); Cooney et al, Science, 241:456 (1988); and Dervan et al., Science, 251: 1360 (1991)), thereby preventing transcription and the production of G-protein chemokine receptor. The antisense RNA oligonucleotide hybridizes to the mRNA in vivo and blocks translation of mRNA molecules into G-protein coupled receptor (antisense—Okano, J. Neurochem., 56:560 (1991); Oligodeoxynucleotides as Antisense Inhibitors of Gene Expression, CRC Press, Boca Raton, Fla. (1988)). The oligonucleotides described above can also be delivered to cells such that the antisense RNA or DNA may be expressed in vivo to inhibit production of G-protein chemokine receptor.

A small molecule which binds to the G-protein chemokine receptor, making it inaccessible to ligands such that normal biological activity is prevented, for example small peptides or peptide-like molecules, may also be used to inhibit activation of the receptor polypeptide of the present invention.

A soluble form of the G-protein chemokine receptor, e.g. a fragment of the receptors, may be used to inhibit activation of the receptor by binding to the ligand to a polypeptide of the present invention and preventing the ligand from interacting with membrane bound G-protein chemokine receptors.

The compounds which bind to and activate the G-protein chemokine receptors of the present invention may be employed to stimulate haematopoiesis, wound healing, coagulation, angiogenesis, to treat solid tumors, chronic infections, leukemia, T-cell mediated auto-immune diseases, parasitic infections, psoriasis, and to stimulate growth factor activity.

The compounds which bind to and inhibit the G-protein chemokine receptors of the present invention may be employed to treat allergy, atherogenesis, anaphylaxis, malignancy, chronic and acute inflammation, histamine and IgE-mediated allergic reactions, prostaglandin-independent fever, bone marrow failure, silicosis, sarcoidosis, rheumatoid arthritis, shock and hyper-eosinophilic syndrome.

The compounds may be employed in combination with a suitable pharmaceutical carrier. Such compositions comprise a therapeutically effective amount of the compound and a pharmaceutically acceptable carrier or excipient. Such a carrier includes but is not limited to saline, buffered saline, dextrose, water, glycerol, ethanol, and combinations thereof. The formulation should suit the mode of administration.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the compounds of the present invention may be employed in conjunction with other therapeutic compounds.

The pharmaceutical compositions may be administered in a convenient manner such as by the topical, intravenous, intraperitoneal, intramuscular, subcutaneous, intranasal or intradermal routes. The pharmaceutical compositions are administered in an amount which is effective for treating and/or prophylaxis of the specific indication. In general, the pharmaceutical compositions will be administered in an amount of at least about 10 μg/kg body weight and in most cases they will be administered in an amount not in excess of about 8 mg/Kg body weight per day. In most cases, the dosage is from about 10 μg/kg to about 1 mg/kg body weight daily, taking into account the routes of administration, symptoms, etc.

The G-protein chemokine receptor polypeptides and antagonists or agonists which are polypeptides, may also be employed in accordance with the present invention by expression of such polypeptides in vivo, which is often referred to as "gene therapy."

Thus, for example, cells from a patient may be engineered with a polynucleotide (DNA or RNA) encoding a polypeptide ex vivo, with the engineered cells then being provided to a patient to be treated with the polypeptide. Such methods are well-known in the art. For example, cells may be engineered by procedures known in the art by use of a retroviral particle containing RNA encoding a polypeptide of the present invention.

Similarly, cells may be engineered in vivo for expression of a polypeptide in vivo by, for example, procedures known in the art. As known in the art, a producer cell for producing a retroviral particle containing RNA encoding the polypeptide of the present invention may be administered to a patient for engineering cells in vivo and expression of the polypeptide in vivo. These and other methods for administering a polypeptide of the present invention by such method should be apparent to those skilled in the art from the teachings of the present invention. For example, the expression vehicle for engineering cells may be other than a retrovirus, for example, an adenovirus which may be used to engineer cells in vivo after combination with a suitable delivery vehicle.

Retroviruses from which the retroviral plasmid vectors hereinabove mentioned may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus, Myeloproliferative Sarcoma Virus, and mammary tumor virus. In one embodiment, the retroviral plasmid vector is derived from Moloney Murine Leukemia Virus.

The vector includes one or more promoters. Suitable promoters which may be employed include, but are not limited to, the retroviral LTR; the SV40 promoter; and the human cytomegalovirus (CMV) promoter described in Miller, et al., *Biotechniques*, Vol. 7, No. 9, 980–990 (1989), or any other promoter (e.g., cellular promoters such as eukaryotic cellular promoters including, but not limited to, the histone, pol III, and β-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding the polypeptide of the present invention is under the control of a suitable promoter. Suitable promoters which may be employed include, but are not limited to, adenoviral promoters, such as the adenoviral major late promoter; or hetorologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs (including the modified retroviral LTRs hereinabove described); the β-actin promoter; and human growth hormone promoters. The promoter also may be the native promoter which controls the genes encoding the polypeptides.

The retroviral plasmid vector is employed to transduce packaging cell lines to form producer cell lines. Examples of packaging cells which may be transfected include, but are not limited to, the PE501, PA317, ψ2, ψ-AM, PA12, T19-14X, VT-19-17-H2, ψCRE, ψCRIP, GP+E-86, GP+envAm12, and DAN cell lines as described in Miller, *Human Gene Therapy*, Vol. 1, pgs. 5–14 (1990), which is incorporated herein by reference in its entirety. The vector may transduce the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line generates infectious retroviral vector particles which include the nucleic acid sequence(s) encoding the polypeptides. Such retroviral vector particles then may be employed, to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

The present invention also provides a method for determining whether a ligand not known to be capable of binding to a G-protein chemokine receptor can bind to such receptor which comprises contacting a mammalian cell which expresses a G-protein chemokine receptor with the ligand under conditions permitting binding of ligands to the G-protein chemokine receptor, detecting the presence of a ligand which binds to the receptor and thereby determining whether the ligand binds to the G-protein chemokine receptor. The systems hereinabove described for determining agonists and/or antagonists may also be employed for determining ligands which bind to the receptor.

This invention also provides a method of detecting expression of a G-protein chemokine receptor polypeptide of the present invention on the surface of a cell by detecting the presence of mRNA coding for the receptor which comprises obtaining total mRNA from the cell and contacting the mRNA so obtained with a nucleic acid probe comprising a nucleic acid molecule of at least 10 nucleotides capable of specifically hybridizing with a sequence included within the sequence of a nucleic acid molecule encoding the receptor under hybridizing conditions, detecting the presence of mRNA hybridized to the probe, and thereby detecting the expression of the receptor by the cell.

The present invention also provides a method for identifying receptors related to the receptor polypeptides of the present invention. These related receptors may be identified by homology to a G-protien chemokine receptor polypeptide of the present invention, by low stringency cross hybridization, or by identifying receptors that interact with related natural or synthetic ligands and or elicit similar behaviors after genetic or pharmacological blockade of the chemokine receptor polypeptides of the present invention.

Fragments of the genes may be used as a hybridization probe for a cDNA library to isolate other genes which have a high sequence similarity to the genes of the present invention, or which have similar biological activity. Probes of this type are at least 20 bases, preferably at least 30 bases and most preferably at least 50 bases or more. The probe may also be used to identify a cDNA clone corresponding to a full length transcript and a genomic clone or clones that contain the complete gene of the present invention including regulatory and promoter regions, exons and introns. An example of a screen of this type comprises isolating the coding region of the gene by using the known DNA sequence to synthesize an oligonucleotide probe. Labeled oligonucleotides having a sequence complementary to that of the genes of the present invention are used to screen a library of human cDNA, genomic DNA or mRNA to determine which members of the library the probe hybridizes to.

The present invention also contemplates the use of the genes of the present invention as a diagnostic, for example, some diseases result from inherited defective genes. These genes can be detected by comparing the sequences of the defective gene with that of a normal one. Subsequently, one can verify that a "mutant" gene is associated with abnormal receptor activity. In addition, one can insert mutant receptor genes into a suitable vector for expression in a functional assay system (e.g., calorimetric assay, expression on MacConkey plates, complementation experiments, in a receptor deficient strain of HEK293 cells) as yet another means to verify or identify mutations. Once "mutant" genes have been identified, one can then screen population for carriers of the "mutant" receptor gene.

Individuals carrying mutations in the gene of the present invention may be detected at the DNA level by a variety of techniques. Nucleic acids used for diagnosis may be obtained from a patient's cells, including but not limited to such as from blood, urine, saliva, tissue biopsy and autopsy material. The genomic DNA may be used directly for detection or may be amplified enzymatically by using PCR (Saiki, et al., *Nature*, 324:163–166 1986) prior to analysis. RNA or cDNA may also be used for the same purpose. As an example, PCR primers complimentary to the nucleic acid of the instant invention can be used to identify and analyze mutations in the gene of the present invention. For example, deletions and insertions can be detected by a change in size of the amplified product in comparison to the normal genotype. Point mutations can be identified by hybridizing amplified DNA to radio labeled RNA of the invention or alternatively, radio labeled antisense DNA sequences of the invention. Perfectly matched sequences can be distinguished from mismatched duplexes by RNase A digestion or by differences in melting temperatures. Such a diagnostic would be particularly useful for prenatal or even neonatal testing.

Sequence differences between the reference gene and "mutants" may be revealed by the direct DNA sequencing method. In addition, cloned DNA segments may be used as probes to detect specific DNA segments. The sensitivity of this method is greatly enhanced when combined with PCR. For example, a sequence primer is used with double stranded PCR product or a single stranded template molecule generated by a modified PCR. The sequence determination is performed by conventional procedures with radio labeled nucleotide or by an automatic sequencing procedure with fluorescent-tags.

Genetic testing based on DNA sequence differences may be achieved by detection of alterations in the electrophoretic mobility of DNA fragments in gels with or without denaturing agents. Sequences changes at specific locations may also be revealed by nucleus protection assays, such RNase and Si protection or the chemical cleavage method (e.g. Cotton, et al., *PNAS, USA*, 85:4397–4401 1985).

In addition, some diseases are a result of, or are characterized by changes in gene expression which can be detected by changes in the mRNA. Alternatively, the genes of the present invention can be used as a reference to identify individuals expressing a decrease of functions associated with receptors of this type.

The present invention also relates to a diagnostic assay for detecting altered levels of soluble forms of the G-proein chemokine receptor polypeptides of the present invention in various tissues. Assays used to detect levels of the soluble receptor polypeptides in a sample derived from a host are well known to those of skill in the art and include radioimmunoassays, competitive-binding assays, Western blot analysis and preferably as ELISA assay.

An ELISA assay initially comprises preparing an antibody specific to antigens of the G-protein chemokine receptor polypeptides, preferably a monoclonal antibody. In addition a reporter antibody is prepared against the monoclonal antibody. To the reporter antibody is attached a detectable reagent such as radioactivity, fluorescence or in this example a horseradish peroxidase enzyme. A sample is now removed from a host and incubated on a solid support, e.g. a polystyrene dish, that binds the proteins in the sample. Any free protein binding sites on the dish are then covered by incubating with a non-specific protein such as bovine serum albumin. Next, the monoclonal antibody is incubated in the dish during which time the monoclonal antibodies attach to any G-protein chemokine receptor proteins attached to the polystyrene dish. All unbound monoclonal antibody is washed out with buffer. The reporter antibody linked to horseradish peroxidase is now placed in the dish resulting in binding of the reporter antibody to any monoclonal antibody bound to G-protein chemokine receptor proteins. Unattached reporter antibody is then washed out. Peroxidase substrates are then added to the dish and the amount of color developed in a given time period is a measurement of the amount of G-protein chemokine receptor proteins present in a given volume of patient sample when compared against a standard curve.

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

Briefly, sequences can be mapped to chromosomes by preparing PCR primers (preferably 15–25 bp) from the cDNA. Computer analysis of the cDNA is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clone to a metaphase chromosomal spread can be used to provide a precise chromosomal location in one step. This technique can be used with cDNA as short as 50 or 60 bases. For a review of this technique, see Verma et al., Human Chromosomes: a Manual of Basic Techniques, Pergamon Press, New York (1988).

Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

An antibody generated against the chemokine receptor may agonize or may antagonize the chemokine receptor.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

For preparation of monoclonal antibodies, any technique which provides antibodies produced by continuous cell line cultures can be used. Examples include the hybridoma technique (Kohler and Milstein, 1975, Nature, 256:495–497), the trioma technique, the human B-cell hybridoma technique (Kozbor et al., 1983, Immunology Today 4:72), and the EBV-hybridoma technique to produce human monoclonal antibodies (Cole, et al., 1985, in Monoclonal Antibodies and Cancer Therapy, Alan R. Liss, Inc., pp. 77–96).

Techniques described for the production of single chain antibodies (U.S. Pat. No. 4,946,778) can be adapted to produce single chain antibodies to immunogenic polypeptide products of this invention. Also, transgenic mice may be used to express humanized antibodies to immunogenic polypeptide products of this invention.

The present invention will be further described with reference to the following examples; however, it is to be understood that the present invention is not limited to such examples. All parts or amounts, unless otherwise specified, are by weight.

In order to facilitate understanding,of the following examples certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 $\mu$g of plasmid or DNA fragment is used with about 2 units of enzyme in about 20 $\mu$l of buffer solution. For the purpose of isolating DNA fragments for plasmid construction, typically 5 to 50 $\mu$g of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D. et al., Nucleic Acids Res., 8:4057 (1980).

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units to T4 DNA ligase ("ligase") per 0.5 µg of approximately equimolar amounts of the DNA fragments to be ligated.

Unless otherwise stated, transformation was performed as described in the method of Graham, F. and Van der Eb, A., Virology, 52:456–457 (1973).

EXAMPLE 1

Bacterial Expression and Purification of HDGNR10

The DNA sequence encoding for HDGNR10, ATCC No. 97183 is initially amplified using PCR oligonucleotide primers corresponding to the 5' and sequences of the processed HDGNR10 protein (minus the signal peptide sequence) and the vector sequences 3' to the HDGNR10 gene. Additional nucleotides corresponding to HDGNR10 were added to the 5' and 3' sequences respectively. The 5' oligonucleotide primer has the sequence 5' CGGAATTCCTCCATGGAT-TATCAAGTGTCA 3' (SEQ ID NO:3) contains an EcoRI restriction enzyme site followed by 18 nucleotides of HDGNR10 coding sequence starting from the presumed terminal amino acid of the processed protein codon. The 3' sequence 5° CGGAAGCTTCGTCACAAGCCCACA-GATAT 3' (SEQ ID NO:4) contains complementary sequences to a HindIII site and is followed by 18 nucleotides of HDGNR10 coding sequence. The restriction enzyme sites correspond to the restriction enzyme sites on the bacterial expression vector pQE-9 (Qiagen, Inc. 9259 Eton Avenue, Chatsworth, Calif., 91311). pQE-9 encodes antibiotic resistance (Amp'), a bacterial origin of replication (ori), an IPTG-regulatable promoter operator (P/O), a ribosome binding site (RBS), a 6-His tag and restriction enzyme sites. pQE-9 was then digested with EcoRI and HindIII. The amplified sequences were ligated into pQE-9 and were inserted in frame with the sequence encoding for the histidine tag and the RBS. The ligation mixture was then used to transform E. coli strain M15/rep 4 (Qiagen, Inc.) by the procedure described in Sambrook, J. et al., Molecular Cloning: A Laboratory Manual, Cold Spring Laboratory Press, (1989). M15/rep4 contains multiple copies of the plasmid pREP4, which expresses the lacI repressor and also confers kanamycin resistance (Kan'). Transformants are identified by their ability to grow on LB plates and ampicillin/kanamycin resistant colonies were selected. Plasmid DNA was isolated and confirmed by restriction analysis. Clones containing the desired constructs were grown overnight (O/N) in liquid culture in LB media supplemented with both Amp (100 ug/ml) and Kan (25 ug/ml). The O/N culture is used to inoculate a large culture at a ratio of 1:100 to 1:250. The cells were grown to an optical density 600 (O.D.$^{600}$) of between 0.4 and 0.6. IPTG ("Isopropyl-B-D-thiogalacto pyranoside") was then added to a final concentration of 1 mM. IPTG induces by inactivating the lacI repressor, clearing the P/O leading to increased gene expression. Cells were grown an extra 3 to 4 hours. Cells were then harvested by centrifugation. The cell pellet was solubilized in the chaotropic agent 6 Molar Guanidine HCl. After clarification, solubilized HDGNR10 was purified from this solution by chromatography on a Nickel-Chelate column under conditions that allow for tight binding by proteins containing the 6-His tag. Hochuli, E. et al., J. Chromatography 411:177–184 (1984). HDGNR10 was eluted from the column in 6 molar guanidine HCl pH 5.0 and for the purpose of renaturation adjusted to 3 molar guanidine HCl, 100 mM sodium phosphate, 10 mmolar glutathione (reduced) and 2 mmolar glutathione (oxidized). After incubation in this solution for 12 hours the protein was dialyzed to 10 mmolar sodium phosphate.

EXAMPLE 2

Expression of Recombinant HDGNR10 in COS Cells

The expression of plasmid, HDGNR10 HA is derived from a vector pcDNAI/Amp (Invitrogen) containing: 1) SV40 origin of replication, 2) ampicillin resistance gene, 3) E.coli replication origin, 4) CKV promoter followed by a polylinker region, a SV40 intron and polyadenylation site. A DNA fragment encoding the entire HDGNR10 precursor and a HA tag fused in frame to its 3' end was cloned into the polylinker region of the vector, therefore, the recombinant protein expression is directed under the CMV promoter. The HA tag correspond to an epitope derived from the influenza hemagglutinin protein as previously described (I. Wilson, H. Niman, R. Heighten, A Cherenson, M. Connolly, and R. Lerner, 1984, Cell 37, 767). The infusion of HA tag to the target protein allows easy detection of the recombinant protein with an antibody that recognizes the HA epitope.

The plasmid construction strategy is described as follows: The DNA sequence encoding for HDGNR10, ATCC No. 97183, was constructed by PCR using two primers: the 5' primer 5' GTCC AAGCTTGCCACCATGGATTAT-CAAGTGTCA 3' (SEQ ID NO:5) and contains a HindIII site followed by 18 nucleotides of HDGNR10 coding sequence starting from the initiation codon; the 3' sequence 5' CTAGCTCGAGTCAAGCGTAGTCTGG-GACGTCGTATGGGTAGCACAAGCCCACA-GATATTTC 3' (SEQ ID NO:6) contains complementary sequences to an XhoI site, translation stop codon, HA tag and the last 18 nucleotides of the HDGNR10 coding sequence (not including the stop codon). Therefore, the PCR product contains a HindIII site HDGNR10 coding sequence followed by HA tag fused in frame, a translation termination stop codon next to the HA tag, and an XhoI site. The PCR amplified DNA fragment and the vector, pcDNAI/Amp, were digested with HindIII and XhoI restriction enzyme and ligated. The ligation mixture was transformed into E. coli strain SURE (available from Stratagene Cloning Systems, 11099 North Torrey Pines Road, La Jolla, Calif. 92037) the transformed culture was plated on ampicillin media plates and resistant colonies were selected. Plasmid DNA was isolated from transformants and examined by restriction analysis for the presence of the correct fragment. For expression of the recombinant HDGNR10, COS cells were transfected with the expression vector by DEAE-DEXTRAN method. (J. Sambrook, E. Fritsch, T. Maniatis, Molecular Cloning: A Laboratory Manual, Cold Spring Laboratory Press, (1989)). The expression of the HDGNR10 HA protein was detected by radiolabelling and immunoprecipitation method. (E. Harlow, D. Lane, Antibodies: A Laboratory Manual, Cold Spring Harbor Laboratory Press, (1988)). Cells were labelled for 8 hours with $^{35}$S-cysteine two days post transfection. Culture media were then collected and cells were lysed with detergent (RIPA buffer (150 mM NaCl, 1% NP-40, 0.1% SDS, 1% NP-40, 0.5% DOC, 50 mM Tris, pH 7.5). (Wilson, I. et al., Id. 37:767 (1984)). Both cell lysate and culture media were precipitated with a HA specific monoclonal antibody. Proteins precipitated were analyzed on 15% SDS-PAGE gels.

EXAMPLE 3

Cloning and Expression of HDGNR10 Using the Baculovirus Expression System

The DNA sequence encoding the full length HDGNR10 protein, ATCC No.97183, was amplified using PCR oligonucleotide primers corresponding to the 5' and 3' sequences of the gene:

The 5' primer has the sequence 5' CGGGATCCCTC-CATGGATTAT CAAGTGTCA 3' (SEQ ID NO:7) and contains a BamHI restriction enzyme site followed by 4 nucleotides resembling an efficient signal for the initiation of translation in eukaryotic cells (J. Mol. Biol. 1987, 196, 947–950, Kozak, M.), and just behind the first 18 nucleotides of the HDGNR10 gene (the initiation codon for translation is "ATG").

The 3' primer has the sequence 5' CGGGATCCCGCT CACAAGCCCACAGATAT 3' (SEQ ID NO:8) and contains the cleavage site for the restriction endonuclease BamHI and 18 nucleotides complementary to the 3' non-translated sequence of the HDGNR10 gene. The amplified sequences were isolated from a 1% agarose gel using a commercially available kit ("Geneclean," BIO 101 Inc., La Jolla, Calif.). The fragment was then digested with the endonuclease BamHI and purified as described above. This fragment is designated F2.

The vector PRG1 (modification of pVL941 vector, discussed below) is used for the expression of the HDGNR10 protein using the baculovirus expression system (for review see: Summers, M. D. and Smith, G. E. 1987, A manual of methods for baculovirus vectors and insect cell culture procedures, Texas Agricultural Experimental Station Bulletin No. 1555). This expression vector contains the strong polyhedrin promoter of the Autographa californica nuclear polyhedrosis virus (AcMNPV) followed by the recognition sites for the restriction endonuclease BamHI. The polyadenylation site of the simian virus (SV)40 is used for efficient polyadenylation. For an easy selection of recombinant viruses the beta-galactosidase gene from E.coli is inserted in the same orientation as the polyhedrin promoter followed by the polyadenylation signal of the polyhedrin gene. The polyhedrin sequences are flanked at both sides by viral sequences for the cell-mediated homologous recombination of co-transfected wild-type viral DNA. Many other baculovirus vectors could be used in place of pRG1 such as pAc373, pVL941 and pAcIM1 (Luckow, V. A. and Summers, M. D., Virology, 170:31–39).

The plasmid was digested with the restriction enzyme BamHI and then dephosphorylated using calf intestinal phosphatase by procedures known in the art. The DNA was then isolated from a 1% agarose gel as described above. This vector DNA is designated V2.

Fragment F2 and the dephosphorylated plasmid V2 were ligated with T4 DNA ligase. E.coli HB101 cells were then transformed and bacteria identified that contained the plasmid (pBacHDGNR10) with the HDGNR10 gene using the enzyme BamHI. The sequence of the cloned fragment was confirmed by DNA sequencing.

5 μg of the plasmid pBacHDGNR10 were co-transfected with 1.0 μg of a commercially available linearized baculovirus ("BaculoGold baculovirus DNA", Pharmingen, San Diego, Calif.) using the lipofection method (Felgner et al. Proc. Natl. Acad. Sci. USA, 84:7413–7417 (1987)).

1 μg of BaculoGold™ virus DNA and 5 μg of the plasid pBacHDGNR10 were mixed in a sterile well of a microtiter plate containing 50 μl of serum free Grace's medium (Life Technologies Inc., Gaithersburg, Md.). Afterwards 10 μl Lipofectin plus 90 μl Grace's medium were added, mixed and incubated for 15 minutes at room temperature. Then the transfection mixture was added drop wise to the Sf9 insect cells (ATCC CRL 1711) seeded in a 35 mm tissue culture plate with 1 ml Grace' medium without serum. The plate was rocked back and forth to mix the newly added solution. The plate was then incubated for 5 hours at 27° C. After 5 hours the transfection solution was removed from the plate and 1 ml of Grace's insect medium supplemented with 10% fetal calf serum was added. The plate was put back into an incubator and cultivation continued at 27° C. for four days.

After four days the supernatant was collected and a plaque assay performed similar as described by Summers and Smith (supra). As a modification an agarose gel with "Blue Gal" (Life Technologies Inc., Gaithersburg) was used which allows an easy isolation of blue stained plaques. (A detailed description of a "plaque assay" can also be found in the user's guide for insect cell culture and baculovirology distributed by Life Technologies Inc., Gaithersburg, page 9–10).

Four days after the serial dilution, the viruses were added to the cells, blue stained plaques were picked with the tip of an Eppendorf pipette. The agar containing the recombinant viruses was then resuspended in an Eppendorf tube containing 200 μl of Grace's medium. The agar was removed by a brief centrifugation and the supernatant containing the recombinant baculoviruses was used to infect Sf9 cells seeded in 35 mm dishes. Four days later the supernatants of these culture dishes were harvested and then stored at 4° C.

Sf9 cells were grown in Grace's medium supplemented with 10% heat-inactivated FBS. The cells were infected with the recombinant baculovirus V-HDGNR10 at a multiplicity of infection (MOI) of 2. Six hours later the medium was removed and replaced with SF900 II medium minus methionine and cysteine (Life Technologies Inc., Gaithersburg). 42 hours later 5 μCi of $^{35}$S-methionine and 5 μCi $^{35}$S cysteine (Amersham) were added. The cells were further incubated for 16 hours before they were harvested by centrifugation and the labelled proteins visualized by SDS-PAGE and autoradiography.

EXAMPLE 4

Expression via Gene Therapy

Fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin, is added. This is then incubated at 37° C. for approximately one week. At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al, DNA, 7:219–25 (1988) flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding a polypeptide of the present invention is amplified using PCR primers which correspond to the 5' and 3' end sequences respectively. The 5' primer contains an EcoRI site and the 3' primer contains a HindIII site. Equal quantities of the Moloney murine sarcoma virus linear backbone and the EcoRI and HindIII fragment are added together, in the presence of T4 DNA ligase. The resulting mixture is maintained under conditions appropriate for ligation of the two fragments. The ligation mixture is used to transform bacteria HB101, which are then plated onto agar-containing kanamycin for the purpose of confirming that the vector had the gene of interest properly inserted.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the gene is then added to the media and the packaging cells are transduced with the vector. The packaging cells now produce infectious viral particles containing the gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his.

The engineered fibroblasts are then injected into the host, either alone or after having been grown to confluence on cytodex 3 microcarrier beads. The fibroblasts now produce the protein product.

Numerous modifications and variations of the present invention are possible in light of the above teachings and, therefore, within the scope of the appended claims, the invention may be practiced otherwise than as particularly described.

SEQUENCE LISTING

<160> NUMBER OF SEQ ID NOS: 9

<210> SEQ ID NO 1
<211> LENGTH: 1414
<212> TYPE: DNA
<213> ORGANISM: Artificial Sequence: Genomic
<220> FEATURE:
<221> NAME/KEY: CDS
<222> LOCATION: (259)..(1314)
<223> OTHER INFORMATION: Description of Artifical Sequence: Genomic

<400> SEQUENCE: 1

```
gtgagatggt gctttcatga attcccccaa caagagccaa gctctccatc tagtggacag        60
ggaagctagc agcaaacctt cccttcacta cgaaacttca ttgcttggcc caaaagagag       120
ttaattcaat gtagacatct atgtaggcaa ttaaaaacct attgatgtat aaaacagttt       180
gcattcatgg agggcaacta aatacattct aggactttat aaaagatcac ttttattta       240 tgcacagggt ggaacaag atg gat tat caa gtg tca agt cca atc tat gac         291
                    Met Asp Tyr Gln Val Ser Ser Pro Ile Tyr Asp
                     1               5                   10 atc aat tat tat aca tcg gag ccc tgc caa aaa atc aat gtg aag caa         339
Ile Asn Tyr Tyr Thr Ser Glu Pro Cys Gln Lys Ile Asn Val Lys Gln
             15                  20                  25 atc gca gcc cgc ctc ctg cct ccg ctc tac tca ctg gtg ttc atc ttt         387
Ile Ala Ala Arg Leu Leu Pro Pro Leu Tyr Ser Leu Val Phe Ile Phe
         30                  35                  40 ggt ttt gtg ggc aac atg ctg gtc atc ctc atc ctg ata aac tgc aaa         435
Gly Phe Val Gly Asn Met Leu Val Ile Leu Ile Leu Ile Asn Cys Lys
     45                  50                  55
```

-continued

```
agg ctg aag agc atg act gac atc tac ctg ctc aac ctg gcc atc tct      483
Arg Leu Lys Ser Met Thr Asp Ile Tyr Leu Leu Asn Leu Ala Ile Ser
 60              65                  70                  75 gac ctg ttt ttc ctt ctt act gtc ccc ttc tgg gct cac tat gct gcc      531
Asp Leu Phe Phe Leu Leu Thr Val Pro Phe Trp Ala His Tyr Ala Ala
             80                  85                  90 gcc cag tgg gac ttt gga aat aca atg tgt caa ctc ttg aca ggg ctc      579
Ala Gln Trp Asp Phe Gly Asn Thr Met Cys Gln Leu Leu Thr Gly Leu
         95                 100                 105 tat ttt ata ggc ttc ttc tct gga atc ttc ttc atc atc ctc ctg aca      627
Tyr Phe Ile Gly Phe Phe Ser Gly Ile Phe Phe Ile Ile Leu Leu Thr
        110                 115                 120 atc gat agg tac ctg gct gtc gtc cat gct gtg ttt gct tta aaa gcc      675
Ile Asp Arg Tyr Leu Ala Val Val His Ala Val Phe Ala Leu Lys Ala
        125                 130                 135 agg acg gtc acc ttt ggg gtg gtg aca agt gtg atc act tgg gtg gtg      723
Arg Thr Val Thr Phe Gly Val Val Thr Ser Val Ile Thr Trp Val Val
140                 145                 150                 155 gct gtg ttt gcg tct ctc cca gga atc atc ttt acc aga tct caa aaa      771
Ala Val Phe Ala Ser Leu Pro Gly Ile Ile Phe Thr Arg Ser Gln Lys
                160                 165                 170 gaa ggt ctt cat tac acc tgc agc tct cat ttt cca tac agt cag tat      819
Glu Gly Leu His Tyr Thr Cys Ser Ser His Phe Pro Tyr Ser Gln Tyr
            175                 180                 185 caa ttc tgg aag aat ttc cag aca tta aag ata gtc atc ttg ggg ctg      867
Gln Phe Trp Lys Asn Phe Gln Thr Leu Lys Ile Val Ile Leu Gly Leu
        190                 195                 200 gtc ctg ccg ctg ctt gtc atg gtc atc tgc tac tcg gga atc cta aaa      915
Val Leu Pro Leu Leu Val Met Val Ile Cys Tyr Ser Gly Ile Leu Lys
205                 210                 215 act ctg ctt cgg tgt cga aat gag aag aag agg cac agg gct gtg agg      963
Thr Leu Leu Arg Cys Arg Asn Glu Lys Lys Arg His Arg Ala Val Arg
220                 225                 230                 235 ctt atc ttc acc atc atg att gtt tat ttt ctc ttc tgg gct ccc tac     1011
Leu Ile Phe Thr Ile Met Ile Val Tyr Phe Leu Phe Trp Ala Pro Tyr
                240                 245                 250 aac att gtc ctt ctc ctg aac acc ttc cag gaa ttc ttt ggc ctg aat     1059
Asn Ile Val Leu Leu Leu Asn Thr Phe Gln Glu Phe Phe Gly Leu Asn
            255                 260                 265 aat tgc agt agc tct aac agg ttg gac caa gct atg cag gtg aca gag     1107
Asn Cys Ser Ser Ser Asn Arg Leu Asp Gln Ala Met Gln Val Thr Glu
        270                 275                 280 act ctt ggg atg acg cac tgc tgc atc aac ccc atc atc tat gcc ttt     1155
Thr Leu Gly Met Thr His Cys Cys Ile Asn Pro Ile Ile Tyr Ala Phe
285                 290                 295 gtc ggg gag aag ttc aga aac tac ctc tta gtc ttc ttc caa aag cac     1203
Val Gly Glu Lys Phe Arg Asn Tyr Leu Leu Val Phe Phe Gln Lys His
300                 305                 310                 315 att gcc aaa cgc ttc tgc aaa tgc tgt tct att ttc cag caa gag gct     1251
Ile Ala Lys Arg Phe Cys Lys Cys Cys Ser Ile Phe Gln Gln Glu Ala
                320                 325                 330 ccc gag cga gca agc tca gtt tac acc cga tcc act gag gag cag gaa     1299
Pro Glu Arg Ala Ser Ser Val Tyr Thr Arg Ser Thr Glu Glu Gln Glu
            335                 340                 345 ata tct gtg ggc ttg tgacacggac tcaagtgggc tggtgaccca gtcagagttg    1354
Ile Ser Val Gly Leu
            350 tgcacatggc ttagtttttca tacacagcct gggctggggg tggggtggaa gaggtctttt  1414
```

-continued

```
<210> SEQ ID NO 2
<211> LENGTH: 352
<212> TYPE: PRT
<213> ORGANISM: Artificial Sequence: Genomic
<220> FEATURE:
<223> OTHER INFORMATION: Deduced Amino Acid Sequence

<400> SEQUENCE: 2

Met Asp Tyr Gln Val Ser Ser Pro Ile Tyr Asp Ile Asn Tyr Tyr Thr
1               5                   10                  15

Ser Glu Pro Cys Gln Lys Ile Asn Val Lys Gln Ile Ala Ala Arg Leu
            20                  25                  30

Leu Pro Pro Leu Tyr Ser Leu Val Phe Ile Phe Gly Phe Val Gly Asn
        35                  40                  45

Met Leu Val Ile Leu Ile Leu Ile Asn Cys Lys Arg Leu Lys Ser Met
    50                  55                  60

Thr Asp Ile Tyr Leu Leu Asn Leu Ala Ile Ser Asp Leu Phe Phe Leu
65                  70                  75                  80

Leu Thr Val Pro Phe Trp Ala His Tyr Ala Ala Ala Gln Trp Asp Phe
                85                  90                  95

Gly Asn Thr Met Cys Gln Leu Leu Thr Gly Leu Tyr Phe Ile Gly Phe
            100                 105                 110

Phe Ser Gly Ile Phe Phe Ile Ile Leu Leu Thr Ile Asp Arg Tyr Leu
        115                 120                 125

Ala Val Val His Ala Val Phe Ala Leu Lys Ala Arg Thr Val Thr Phe
    130                 135                 140

Gly Val Val Thr Ser Val Ile Thr Trp Val Val Ala Val Phe Ala Ser
145                 150                 155                 160

Leu Pro Gly Ile Ile Phe Thr Arg Ser Gln Lys Glu Gly Leu His Tyr
                165                 170                 175

Thr Cys Ser Ser His Phe Pro Tyr Ser Gln Tyr Gln Phe Trp Lys Asn
            180                 185                 190

Phe Gln Thr Leu Lys Ile Val Ile Leu Gly Leu Val Leu Pro Leu Leu
        195                 200                 205

Val Met Val Ile Cys Tyr Ser Gly Ile Leu Lys Thr Leu Leu Arg Cys
    210                 215                 220

Arg Asn Glu Lys Lys Arg His Arg Ala Val Arg Leu Ile Phe Thr Ile
225                 230                 235                 240

Met Ile Val Tyr Phe Leu Phe Trp Ala Pro Tyr Asn Ile Val Leu Leu
                245                 250                 255

Leu Asn Thr Phe Gln Glu Phe Phe Gly Leu Asn Asn Cys Ser Ser Ser
            260                 265                 270

Asn Arg Leu Asp Gln Ala Met Gln Val Thr Glu Thr Leu Gly Met Thr
        275                 280                 285

His Cys Cys Ile Asn Pro Ile Ile Tyr Ala Phe Val Gly Glu Lys Phe
    290                 295                 300

Arg Asn Tyr Leu Leu Val Phe Phe Gln Lys His Ile Ala Lys Arg Phe
305                 310                 315                 320

Cys Lys Cys Cys Ser Ile Phe Gln Gln Glu Ala Pro Glu Arg Ala Ser
                325                 330                 335

Ser Val Tyr Thr Arg Ser Thr Glu Glu Gln Glu Ile Ser Val Gly Leu
            340                 345                 350

<210> SEQ ID NO 3
<211> LENGTH: 30
```

-continued

```
<212> TYPE: DNA
<213> ORGANISM: Oligonucleotide

<400> SEQUENCE: 3
cggaattcct ccatggatta tcaagtgtca                                   30

<210> SEQ ID NO 4
<211> LENGTH: 29
<212> TYPE: DNA
<213> ORGANISM: Oligonucleotide

<400> SEQUENCE: 4
cggaagcttc gtcacaagcc cacagatat                                    29

<210> SEQ ID NO 5
<211> LENGTH: 34
<212> TYPE: DNA
<213> ORGANISM: Oligonucleotide

<400> SEQUENCE: 5
gtccaagctt gccaccatgg attatcaagt gtca                              34

<210> SEQ ID NO 6
<211> LENGTH: 61
<212> TYPE: DNA
<213> ORGANISM: Oligonucleotide

<400> SEQUENCE: 6
ctagctcgag tcaagcgtag tctgggacgt cgtatgggta gcacaagccc acagatattt  60
c                                                                 61

<210> SEQ ID NO 7
<211> LENGTH: 30
<212> TYPE: DNA
<213> ORGANISM: Oligonucleotide

<400> SEQUENCE: 7
cgggatccct ccatggatta tcaagtgtca                                   30

<210> SEQ ID NO 8
<211> LENGTH: 29
<212> TYPE: DNA
<213> ORGANISM: Oligonucleotide

<400> SEQUENCE: 8
cgggatcccg ctcacaagcc cacagatat                                    29

<210> SEQ ID NO 9
<211> LENGTH: 329
<212> TYPE: PRT
<213> ORGANISM: Protein

<400> SEQUENCE: 9

Glu Glu Val Thr Thr Phe Phe Asp Tyr Asp Tyr Gly Ala Pro Cys His
1               5                   10                  15

Lys Phe Asp Val Lys Gln Ile Gly Ala Gln Leu Leu Pro Pro Leu Tyr
            20                  25                  30

Ser Leu Val Phe Ile Phe Gly Phe Val Gly Asn Met Leu Val Val Leu
        35                  40                  45

Ile Leu Ile Asn Cys Lys Lys Leu Lys Cys Leu Thr Asp Ile Tyr Leu
    50                  55                  60
```

-continued

```
Leu Asn Leu Ala Ile Ser Asp Leu Leu Phe Leu Ile Thr Leu Pro Leu
 65              70                  75                  80

Trp Ala His Ser Ala Ala Asn Glu Trp Val Phe Gly Asn Ala Met Cys
                 85                  90                  95

Lys Leu Phe Thr Gly Leu Tyr His Ile Arg Tyr Leu Ala Ile Val His
                100                 105                 110

Ala Val Phe Ala Leu Lys Ala Arg Thr Val Thr Phe Gly Val Val Thr
                115                 120                 125

Ser Val Ile Thr Trp Leu Val Ala Val Phe Ala Ser Val Pro Gly Ile
                130                 135                 140

Ile Phe Thr Lys Cys Gln Lys Glu Asp Ser Val Tyr Val Cys Gly Pro
145                 150                 155                 160

Tyr Phe Pro Arg Gly Trp Asn Asn Phe His Thr Ile Met Arg Asn Ile
                165                 170                 175

Leu Gly Leu Val Leu Pro Leu Leu Ile Met Val Ile Cys Tyr Ser Gly
                180                 185                 190

Ile Leu Lys Thr Leu Leu Arg Cys Arg Asn Glu Lys Lys Arg His Arg
            195                 200                 205

Ala Val Arg Val Ile Phe Thr Ile Met Ile Val Tyr Phe Leu Phe Trp
            210                 215                 220

Thr Pro Tyr Asn Ile Val Ile Leu Leu Asn Thr Phe Gln Glu Phe Phe
225                 230                 235                 240

Gly Leu Ser Asn Cys Glu Ser Thr Ser Gln Leu Asp Gln Ala Thr Gln
                245                 250                 255

Val Thr Glu Thr Leu Gly Met Thr His Cys Cys Ile Asn Pro Ile Ile
                260                 265                 270

Tyr Ala Phe Val Gly Glu Lys Phe Arg Ser Leu Phe His Ile Ala Leu
            275                 280                 285

Gly Cys Arg Ile Ala Pro Leu Gln Lys Pro Val Cys Gly Gly Pro Gly
    290                 295                 300

Val Arg Pro Gly Lys Asn Val Lys Val Thr Thr Gln Gly Leu Leu Asp
305                 310                 315                 320

Gly Arg Gly Lys Gly Lys Ser Ile Gly
                325
```

What is claimed is:

1. An isolated antibody which binds a fragment of the polypeptide of SEQ ID NO:2, wherein said fragment consists of an extracellular portion cleaved from the transmembrane and intracellular domain of said polypeptide.

2. The antibody of claim 1, wherein said antibody binds the whole native polypeptide of SEQ ID NO:2.

3. The antibody of claim 1, wherein said antibody is polyclonal.

4. The antibody of claim 1, wherein said antibody is monoclonal.

5. The antibody of claim 1, wherein said antibody is chimeric.

6. The antibody of claim 1, wherein said antibody is humanized.

7. The antibody of claim 1, wherein said antibody is an antagonist of the polypeptide of SEQ ID NO:2.

8. The antibody of claim 1, wherein said antibody is an agonist of the polypeptide of SEQ ID NO:2.

9. A composition comprising the antibody of claim 1, and a carrier.

10. A method of producing the antibody of claim 1, comprising:

(a) immunizing an animal with a polypeptide comprising an extracellular portion cleaved from the transmembrane and intracellular domain of SEQ ID NO:2; and (b) producing an antibody which binds said polypeptide.

11. An isolated antibody fragment which binds a fragment of the polypeptide of SEQ ID NO:2, wherein said polypeptide fragment consists of an extracellular portion cleaved from the transmembrane and intracellular domain of said polypeptide.

12. The antibody fragment of claim 11, wherein said antibody fragment binds the whole native polypeptide of SEQ ID NO:2.

13. The antibody fragment of claim 11, wherein said antibody fragment comprises an Fab fragment.

14. The antibody fragment of claim 11, wherein said antibody fragment comprises a single chain antibody.

15. The antibody fragment of claim 11, wherein said antibody fragment is chimeric.

16. The antibody fragment of claim 11, wherein said antibody fragment is humanized.

17. The antibody fragment of claim 11, wherein said antibody fragment is an antagonist of the polypeptide of SEQ ID NO:2.

18. The antibody fragment of claim 11, wherein said antibody fragment is an agonist of the polypeptide of SEQ ID NO:2.

19. A composition comprising the antibody fragment of claim 11, and a carrier.

20. A method of producing the antibody fragment of claim 11, comprising:
  (a) immunizing an animal with a polypeptide comprising an extracellular portion cleaved from the transmembrane and intracellular domain of SEQ ID NO:2; and
  (b) producing an antibody fragment which binds said polypeptide.

21. An isolated antibody which binds a fragment of the HDGNR10 polypeptide encoded by the HDGNR10 clone in ATCC Deposit No. 97183, wherein said fragment consists of an extracellular portion cleaved from the transmembrane and intracellular domain of said polypeptide.

22. The antibody of claim 21, wherein said antibody binds the whole native polypeptide encoded by the HDGNR10 clone in ATCC Deposit No. 97183.

23. The antibody of claim 21, wherein said antibody is polyclonal.

24. The antibody of claim 21, wherein said antibody is monoclonal.

25. The antibody of claim 21, wherein said antibody is chimeric.

26. The antibody of claim 21, wherein said antibody is humanized.

27. The antibody of claim 21, wherein said antibody is an antagonist of the polypeptide encoded by the HDGNR10 clone in ATCC Deposit No. 97183.

28. The antibody of claim 21, wherein said antibody is an agonist of the polypeptide encoded by the HDGNR10 clone in ATCC Deposit No. 97183.

29. A composition comprising the antibody of claim 21, and a carrier.

30. A method of producing the antibody of claim 21, comprising:
  (a) immunizing an animal with a polypeptide comprising an extracellular portion cleaved from the transmembrane and intracellular domain of the HDGNR10 amino acid sequence encoded by the HDGNR10 clone in ATCC Deposit No. 97183; and
  (b) producing an antibody which binds said polypeptide.

31. An isolated antibody fragment which binds a fragment of the HDGNR10 polypeptide encoded by the HDGNR10 clone in ATCC Deposit No. 97183, wherein said polypeptide fragment consists of an extracellular portion cleaved from the transmembrane and intracellular domain of said polypeptide.

32. The antibody fragment of claim 31, wherein said antibody fragment binds the whole native polypeptide encoded by the HDGNR10 clone in ATCC Deposit No. 97183.

33. The antibody fragment of claim 31, wherein said antibody fragment comprises an Fab fragment.

34. The antibody fragment of claim 31, wherein said antibody fragment comprises a single chain antibody.

35. The antibody fragment of claim 31, wherein said antibody fragment is chimeric.

36. The antibody fragment of claim 31, wherein said antibody fragment is humanized.

37. The antibody fragment of claim 31, wherein said antibody fragment is an antagonist of the polypeptide encoded by the HDGNR10 clone in ATCC Deposit No. 97183.

38. The antibody fragment of claim 31, wherein said antibody fragment is an agonist of the polypeptide encoded by the HDGNR10 clone in ATCC Deposit No. 97183.

39. A composition comprising the antibody fragment of claim 31, and a carrier.

40. A method of producing the antibody fragment of claim 31, comprising:
  (a) immunizing an animal with a polypeptide comprising an extracellular portion cleaved from the transmembrane and intracellular domain of the HDGNR10 amino acid sequence encoded by the HDGNR10 clone in ATCC Deposit No. 97183; and
  (b) producing an antibody fragment which binds said polypeptide.

41. An isolated antibody which binds the polypeptide of SEQ ID NO:2 when said polypeptide is expressed on the surface of a cell.

42. The antibody of claim 41, wherein said antibody binds an extracellular portion cleaved from the transmembrane and intracellular domain of the polypeptide of SEQ ID NO:2.

43. The antibody of claim 41, wherein said antibody is polyclonal.

44. The antibody of claim 41, wherein said antibody is monoclonal.

45. The antibody of claim 41, wherein said antibody is chimeric.

46. The antibody of claim 41, wherein said antibody is humanized.

47. The antibody of claim 41, wherein said antibody is an antagonist of the polypeptide of SEQ ID NO:2.

48. The antibody of claim 41, wherein said antibody is an agonist of the polypeptide of SEQ ID NO:2.

49. A composition comprising the antibody of claim 41, and a carrier.

50. A method of producing the antibody of claim 41, comprising:
  (a) immunizing an animal with a polypeptide comprising an extracellular portion cleaved from the transmembrane and intracellular domain of SEQ ID NO:2; and
  (b) producing an antibody which binds said polypeptide.

51. An isolated antibody fragment which binds the polypeptide of SEQ ID NO:2 when said polypeptide is expressed on the surface of a cell.

52. The antibody fragment of claim 51, wherein said antibody fragment binds an extracellular portion cleaved from the transmembrane and intracellular domain of the polypeptide of SEQ ID NO:2.

53. The antibody fragment of claim 51, wherein said antibody fragment comprises an Fab fragment.

54. The antibody fragment of claim 51, wherein said antibody fragment comprises a single chain antibody.

55. The antibody fragment of claim 51, wherein said antibody fragment is chimeric.

56. The antibody fragment of claim 51, wherein said antibody fragment is humanized.

57. The antibody fragment of claim 51, wherein said antibody fragment is an antagonist of the polypeptide of SEQ ID NO:2.

58. The antibody fragment of claim 51, wherein said antibody fragment is an agonist of the polypeptide of SEQ ID NO:2.

59. A composition comprising the antibody fragment of claim 51, and a carrier.

60. A method of producing the antibody fragment of claim 51, comprising:
  (a) immunizing an animal with a polypeptide comprising an extracellular portion cleaved from the transmembrane and intracellular domain of SEQ ID NO:2; and (b) producing an antibody fragment which binds said polypeptide.

61. An isolated antibody which binds the HDGNR10 polypeptide encoded by the HDGNR10 clone in ATCC Deposit No. 97183 when said polypeptide is expressed on the surface of a cell.

62. The antibody of claim 61, wherein said antibody binds an extracellular portion cleaved from the transmembrane and intracellular domain of the HDGNR10 polypeptide encoded by the HDGNR10 clone in ATCC Deposit No. 97183.

63. The antibody of claim 61, wherein said antibody is polyclonal.

64. The antibody of claim 61, wherein said antibody is monoclonal.

65. The antibody of claim 61, wherein said antibody is chimeric.

66. The antibody of claim 61, wherein said antibody is humanized.

67. The antibody of claim 61, wherein said antibody is an antagonist of the HDGNR10 polypeptide encoded by the HDGNR10 clone in ATCC Deposit No. 97183.

68. The antibody of claim 61, wherein said antibody is an agonist of the HDGNR10 polypeptide encoded by the HDGNR10 clone in ATCC Deposit No. 97183.

69. A composition comprising the antibody of claim 61, and a carrier.

70. A method of producing the antibody of claim 61, comprising:

(a) immunizing an animal with a polypeptide comprising an extracellular portion cleaved from the transmembrane and intracellular domain of the HDGNR10 amino acid sequence encoded by the HDGNR10 clone in ATCC Deposit No. 97183; and (b) producing an antibody which binds said polypeptide.

71. An isolated antibody fragment which binds the HDGNR10 polypeptide encoded by the HDGNR10 clone in ATCC Deposit No. 97183 when said polypeptide is expressed on the surface of a cell.

72. The antibody fragment of claim 71, wherein said antibody fragment binds an extracellular portion cleaved from the transmembrane and intracellular domain of the HDGNR10 polypeptide encoded by the HDGNR10 clone in ATCC Deposit No. 97183.

73. The antibody fragment of claim 71, wherein said antibody fragment comprises an Fab fragment.

74. The antibody fragment of claim 71, wherein said antibody fragment comprises a single chain antibody.

75. The antibody fragment of claim 71, wherein said antibody fragment is chimeric.

76. The antibody fragment of claim 71, wherein said antibody fragment is humanized.

77. The antibody fragment of claim 71, wherein said antibody fragment is an antagonist of the HDGNR10 polypeptide encoded by the HDGNR10 clone in ATCC Deposit No. 97183.

78. The antibody fragment of claim 71, wherein said antibody fragment is an agonist of the HDGNR10 polypeptide encoded by the HDGNR10 clone in ATCC Deposit No. 97183.

79. A composition comprising the antibody fragment of claim 71, and a carrier.

80. A method of producing the antibody fragment of claim 71, comprising:

(a) immunizing an animal with a polypeptide comprising an extracellular portion cleaved from the transmembrane and intracellular domain of the HDGNR10 amino acid sequence encoded by the HDGNR10 clone in ATCC Deposit No. 97183; and (b) producing an antibody fragment which binds said polypeptide.

81. The antibody of claim 1, wherein said fragment is fused to a heterologous polypeptide.

82. The antibody fragment of claim 11, said polypeptide fragment is fused to a heterologous polypeptide.

83. The antibody of claim 21, wherein said fragment is fused to a heterologous polypeptide.

84. The antibody fragment of claim 31, wherein said polypeptide fragment is fused to a heterologous polypeptide.

* * * * *

UNITED STATES PATENT AND TRADEMARK OFFICE
CERTIFICATE OF CORRECTION

PATENT NO. : 6,759,519 B2
DATED : July 6, 2004
INVENTOR(S) : Li et al.

It is certified that error appears in the above-identified patent and that said Letters Patent is hereby corrected as shown below:

Title page,
Item [62], Related U.S. Application Data, please delete lines 16-17 and insert therein -- Division of U.S. Appl. No. 09/195,662, filed November 18, 1998; said 09/195,662 is a divisional of U.S. Appl. No. 08/466,343, filed June 6, 1995, now U.S. Patent No. 6,025,154 --.
Item [56], References Cited, FOREIGN PATENT DOCUMENTS, please delete "2128308" and insert therein -- 2128208; -- also delete "SU" and insert therein -- RU --.

Column 1,
Lines 4-7, please delete and insert therein -- The present application is a divisional of U.S. Appl. No. 09/195,662 filed November 18, 1998; said 09/195,662 is a divisional of U.S. Appl. No. 08/466,343, filed June 6, 1995, now U.S. Patent No. 6,025,154, which disclosure is hereby incorporated by reference --.

Signed and Sealed this

Sixteenth Day of November, 2004

JON W. DUDAS
*Director of the United States Patent and Trademark Office*